US011439829B2

(12) United States Patent
Borlase et al.

(10) Patent No.: US 11,439,829 B2
(45) Date of Patent: Sep. 13, 2022

(54) CLINICIAN PROGRAMMER METHODS AND SYSTEMS FOR MAINTAINING TARGET OPERATING TEMPERATURES

(71) Applicant: Axonics, Inc., Irvine, CA (US)

(72) Inventors: Charles Borlase, Lake Forest, CA (US); Prabodh Mathur, Laguna Niguel, CA (US)

(73) Assignee: AXONICS, INC., Irvine, CA (US)

( * ) Notice: Subject to any disclaimer, the term of this patent is extended or adjusted under 35 U.S.C. 154(b) by 182 days.

(21) Appl. No.: 16/882,295

(22) Filed: May 22, 2020

(65) Prior Publication Data

US 2020/0368533 A1    Nov. 26, 2020

Related U.S. Application Data

(60) Provisional application No. 62/852,805, filed on May 24, 2019.

(51) Int. Cl.
*A61N 1/36*        (2006.01)
*G09G 3/36*        (2006.01)

(52) U.S. Cl.
CPC ....... *A61N 1/36142* (2013.01); *A61N 1/3603* (2017.08); *G09G 3/36* (2013.01);
(Continued)

(58) Field of Classification Search
CPC ............ A61N 1/36142; A61N 1/3603; G09G 2320/041; G09G 2320/0626
See application file for complete search history.

(56) References Cited

U.S. PATENT DOCUMENTS 3,057,356 A    10/1962    Greatbatch
3,348,548 A    10/1967    Chardack
(Continued)

FOREIGN PATENT DOCUMENTS

AT    520440     9/2011
AU    4664800    11/2000
(Continued)

OTHER PUBLICATIONS

US 9,601,939 B2, 03/2017, Cong et al. (withdrawn)
(Continued)

*Primary Examiner* — Amanda K Hulbert
*Assistant Examiner* — Philip C Edwards
(74) *Attorney, Agent, or Firm* — Kilpatrick Townsend & Stockton LLP

(57) ABSTRACT

Methods and systems for monitoring and regulating temperatures of neurostimulator programmers are provided herein. A neurostimulator programmer may include one or more sensors that may detect one or more temperatures associated with the neurostimulator programmer. Each of the one or more sensors may be associated with one or more respective threshold values. When these threshold values are exceeded, one or more courses of actions may be taken by the neurostimulator programmer. For example, the neurostimulator programmer may reduce functionality of one or more heat-generating components, increase monitoring of temperature, and/or initiate shutdown of the neurostimulator programmer. In some cases, two or more such methods may be performed simultaneously, for example, one method to deal with high temperatures and another method to deal with particularly excessive temperatures.

28 Claims, 11 Drawing Sheets

(52) U.S. Cl.
CPC .............. *G09G 2320/041* (2013.01); *G09G 2320/0606* (2013.01); *G09G 2320/0626* (2013.01); *G09G 2354/00* (2013.01)

(56) References Cited

U.S. PATENT DOCUMENTS

| | | | |
|---|---|---|---|
| 3,646,940 A | 3/1972 | Timm et al. | |
| 3,824,129 A | 7/1974 | Fagan, Jr. | |
| 3,825,015 A | 7/1974 | Berkovits | |
| 3,888,260 A | 6/1975 | Fischell | |
| 3,902,501 A | 9/1975 | Citron et al. | |
| 3,939,843 A | 2/1976 | Smyth | |
| 3,942,535 A | 3/1976 | Schulman | |
| 3,970,912 A | 7/1976 | Hoffman | |
| 3,995,623 A | 12/1976 | Blake et al. | |
| 4,019,518 A | 4/1977 | Maurer et al. | |
| 4,044,774 A | 8/1977 | Corbin et al. | |
| 4,082,097 A | 4/1978 | Mann et al. | |
| 4,141,365 A | 2/1979 | Fischell et al. | |
| 4,166,469 A | 9/1979 | Littleford | |
| 4,210,383 A | 7/1980 | Davis | |
| 4,269,198 A | 5/1981 | Stokes | |
| 4,285,347 A | 8/1981 | Hess | |
| 4,340,062 A | 7/1982 | Thompson et al. | |
| 4,379,462 A | 4/1983 | Borkan et al. | |
| 4,407,303 A | 10/1983 | Akerstrom | |
| 4,437,475 A | 3/1984 | White | |
| 4,512,351 A | 4/1985 | Pohndorf | |
| 4,550,731 A | 11/1985 | Batina et al. | |
| 4,558,702 A | 12/1985 | Barreras et al. | |
| 4,654,880 A | 3/1987 | Sontag | |
| 4,662,382 A | 5/1987 | Sluetz et al. | |
| 4,719,919 A | 1/1988 | Marchosky et al. | |
| 4,721,118 A | 1/1988 | Harris | |
| 4,722,353 A | 2/1988 | Sluetz | |
| 4,744,371 A | 5/1988 | Harris | |
| 4,800,898 A | 1/1989 | Hess et al. | |
| 4,848,352 A | 7/1989 | Pohndorf et al. | |
| 4,860,446 A | 8/1989 | Lessar et al. | |
| 4,957,118 A | 9/1990 | Erlebacher | |
| 4,989,617 A | 2/1991 | Memberg et al. | |
| 5,012,176 A | 4/1991 | Laforge | |
| 5,052,407 A | 10/1991 | Hauser et al. | |
| 5,197,466 A | 3/1993 | Marchosky et al. | |
| 5,204,611 A | 4/1993 | Nor et al. | |
| 5,255,691 A | 10/1993 | Otten | |
| 5,257,634 A | 11/1993 | Kroll | |
| 5,342,408 A | 8/1994 | deCoriolis et al. | |
| 5,439,485 A | 8/1995 | Mar et al. | |
| 5,476,499 A | 12/1995 | Hirschberg | |
| 5,484,445 A | 1/1996 | Knuth | |
| 5,571,148 A | 11/1996 | Loeb et al. | |
| 5,592,070 A | 1/1997 | Mino | |
| 5,637,981 A | 6/1997 | Nagai et al. | |
| 5,676,162 A | 10/1997 | Larson, Jr. et al. | |
| 5,690,693 A | 11/1997 | Wang et al. | |
| 5,702,428 A | 12/1997 | Tippey et al. | |
| 5,702,431 A | 12/1997 | Wang et al. | |
| 5,712,795 A | 1/1998 | Layman et al. | |
| 5,713,939 A | 2/1998 | Nedungadi et al. | |
| 5,733,313 A | 3/1998 | Barreras, Sr. et al. | |
| 5,735,887 A | 4/1998 | Barreras, Sr. et al. | |
| 5,741,316 A | 4/1998 | Chen et al. | |
| 5,871,532 A | 2/1999 | Schroeppel | |
| 5,876,423 A | 3/1999 | Braun | |
| 5,902,331 A | 5/1999 | Bonner et al. | |
| 5,948,006 A | 9/1999 | Mann | |
| 5,949,632 A | 9/1999 | Barreras, Sr. et al. | |
| 5,957,965 A | 9/1999 | Moumane et al. | |
| 5,991,665 A | 11/1999 | Wang et al. | |
| 6,014,588 A | 1/2000 | Fitz | |
| 6,027,456 A | 2/2000 | Feler et al. | |
| 6,035,237 A | 3/2000 | Schulman et al. | |
| 6,052,624 A | 4/2000 | Mann | |
| 6,055,456 A | 4/2000 | Gerber | |
| 6,057,513 A | 5/2000 | Ushikoshi et al. | |
| 6,067,474 A | 5/2000 | Schulman et al. | |
| 6,075,339 A | 6/2000 | Reipur et al. | |
| 6,076,017 A | 6/2000 | Taylor et al. | |
| 6,081,097 A | 6/2000 | Seri et al. | |
| 6,083,247 A | 7/2000 | Rutten et al. | |
| 6,104,957 A | 8/2000 | Alo et al. | |
| 6,104,960 A | 8/2000 | Duysens et al. | |
| 6,138,681 A | 10/2000 | Chen et al. | |
| 6,157,861 A | 12/2000 | Faltys et al. | |
| 6,165,180 A | 12/2000 | Cigaina et al. | |
| 6,166,518 A | 12/2000 | Echarri et al. | |
| 6,169,387 B1 | 1/2001 | Kaib | |
| 6,172,556 B1 | 1/2001 | Prentice | |
| 6,178,353 B1 | 1/2001 | Griffith et al. | |
| 6,181,105 B1 | 1/2001 | Cutolo et al. | |
| 6,181,961 B1 | 1/2001 | Prass | |
| 6,191,365 B1 | 2/2001 | Avellanet | |
| 6,208,894 B1 | 3/2001 | Schulman et al. | |
| 6,212,430 B1 | 4/2001 | Kung | |
| 6,212,431 B1 | 4/2001 | Hahn et al. | |
| 6,221,513 B1 | 4/2001 | Lasater | |
| 6,227,204 B1 | 5/2001 | Baumann et al. | |
| 6,243,608 B1 | 6/2001 | Pauly et al. | |
| 6,246,911 B1 | 6/2001 | Seligman | |
| 6,249,703 B1 | 6/2001 | Stanton et al. | |
| 6,265,789 B1 | 7/2001 | Honda et al. | |
| 6,275,737 B1 | 8/2001 | Mann | |
| 6,278,258 B1 | 8/2001 | Echarri et al. | |
| 6,305,381 B1 | 10/2001 | Weijand et al. | |
| 6,306,100 B1 | 10/2001 | Prass | |
| 6,314,325 B1 | 11/2001 | Fitz | |
| 6,315,721 B2 | 11/2001 | Schulman et al. | |
| 6,316,909 B1 | 11/2001 | Honda et al. | |
| 6,321,118 B1 | 11/2001 | Hahn | |
| 6,324,432 B1 | 11/2001 | Rigaux et al. | |
| 6,327,504 B1 | 12/2001 | Dolgin et al. | |
| 6,354,991 B1 | 3/2002 | Gross et al. | |
| 6,360,750 B1 | 3/2002 | Gerber et al. | |
| 6,381,496 B1 | 4/2002 | Meadows et al. | |
| 6,393,325 B1 | 5/2002 | Mann et al. | |
| 6,438,423 B1 | 8/2002 | Rezai et al. | |
| 6,442,434 B1 | 8/2002 | Zarinetchi et al. | |
| 6,453,198 B1 | 9/2002 | Torgerson et al. | |
| 6,466,817 B1 | 10/2002 | Kaula et al. | |
| 6,473,652 B1 | 10/2002 | Sarwal et al. | |
| 6,500,141 B1 | 12/2002 | Irion et al. | |
| 6,505,075 B1 | 1/2003 | Weiner | |
| 6,505,077 B1 | 1/2003 | Kast et al. | |
| 6,510,347 B2 | 1/2003 | Borkan | |
| 6,516,227 B1 | 2/2003 | Meadows et al. | |
| 6,517,227 B2 | 2/2003 | Stidham et al. | |
| 6,542,846 B1 | 4/2003 | Miller et al. | |
| 6,553,263 B1 | 4/2003 | Meadows et al. | |
| 6,584,355 B2 | 6/2003 | Stessman | |
| 6,587,728 B2 | 7/2003 | Fang et al. | |
| 6,600,954 B2 | 7/2003 | Cohen et al. | |
| 6,609,031 B1 | 8/2003 | Law et al. | |
| 6,609,032 B1 | 8/2003 | Woods et al. | |
| 6,609,945 B2 | 8/2003 | Jimenez et al. | |
| 6,625,494 B2 | 9/2003 | Fang et al. | |
| 6,652,449 B1 | 11/2003 | Gross et al. | |
| 6,654,634 B1 | 11/2003 | Prass | |
| 6,662,051 B1 | 12/2003 | Eraker et al. | |
| 6,662,053 B2 | 12/2003 | Borkan | |
| 6,664,763 B2 | 12/2003 | Echarri et al. | |
| 6,678,563 B2 | 1/2004 | Fang et al. | |
| 6,685,638 B1 | 2/2004 | Taylor et al. | |
| 6,701,189 B2 | 3/2004 | Fang et al. | |
| 6,721,603 B2 | 4/2004 | Zabara et al. | |
| 6,735,474 B1 | 5/2004 | Loeb et al. | |
| 6,745,077 B1 | 6/2004 | Griffith et al. | |
| 6,809,701 B2 | 10/2004 | Amundson et al. | |
| 6,836,684 B1 | 12/2004 | Rijkhoff et al. | |
| 6,836,685 B1 | 12/2004 | Fitz | |
| 6,847,849 B2 | 1/2005 | Mamo et al. | |
| 6,871,099 B1 | 3/2005 | Whitehurst et al. | |
| 6,892,098 B2 | 5/2005 | Ayal et al. | |
| 6,895,280 B2 | 5/2005 | Meadows et al. | |

(56) References Cited

U.S. PATENT DOCUMENTS

| | | |
|---|---|---|
| 6,896,651 B2 | 5/2005 | Gross et al. |
| 6,901,287 B2 | 5/2005 | Davis et al. |
| 6,907,293 B2 | 6/2005 | Grill et al. |
| 6,923,814 B1 | 8/2005 | Hildebrand et al. |
| 6,941,171 B2 | 9/2005 | Mann et al. |
| 6,959,215 B2 | 10/2005 | Gliner et al. |
| 6,971,393 B1 | 12/2005 | Mamo et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,010,351 B2 | 3/2006 | Firlik et al. |
| 7,024,247 B2 | 4/2006 | Gliner et al. |
| 7,047,078 B2 | 5/2006 | Boggs, II et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,127,298 B1 | 10/2006 | He et al. |
| 7,131,996 B2 | 11/2006 | Wasserman et al. |
| 7,142,925 B1 | 11/2006 | Bhadra et al. |
| 7,146,217 B2 | 12/2006 | Firlik et al. |
| 7,146,219 B2 | 12/2006 | Sieracki et al. |
| 7,151,914 B2 | 12/2006 | Brewer |
| 7,167,743 B2 | 1/2007 | Heruth et al. |
| 7,167,749 B2 | 1/2007 | Biggs et al. |
| 7,167,756 B1 | 1/2007 | Torgerson et al. |
| 7,177,677 B2 | 2/2007 | Kaula et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,214,197 B2 | 5/2007 | Prass |
| 7,216,001 B2 | 5/2007 | Hacker et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,236,831 B2 | 6/2007 | Firlik et al. |
| 7,239,918 B2 | 7/2007 | Strother et al. |
| 7,245,972 B2 | 7/2007 | Davis |
| 7,283,867 B2 | 10/2007 | Strother et al. |
| 7,286,880 B2 | 10/2007 | Olson et al. |
| 7,295,878 B1 | 11/2007 | Meadows et al. |
| 7,299,096 B2 | 11/2007 | Balzer et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,326,181 B2 | 2/2008 | Katims |
| 7,328,068 B2 | 2/2008 | Spinelli et al. |
| 7,330,764 B2 | 2/2008 | Swoyer et al. |
| 7,337,006 B2 | 2/2008 | Kim et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,395,113 B2 | 7/2008 | Heruth et al. |
| 7,396,265 B2 | 7/2008 | Darley et al. |
| 7,406,351 B2 | 7/2008 | Wesselink |
| 7,415,308 B2 | 8/2008 | Gerber et al. |
| 7,444,181 B2 | 10/2008 | Shi et al. |
| 7,444,184 B2 | 10/2008 | Boveja et al. |
| 7,447,546 B2 | 11/2008 | Kim et al. |
| 7,450,991 B2 | 11/2008 | Smith et al. |
| 7,450,993 B2 | 11/2008 | Kim et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,747 B2 | 1/2009 | Gliner et al. |
| 7,483,752 B2 | 1/2009 | Von Arx et al. |
| 7,486,048 B2 | 2/2009 | Tsukamoto et al. |
| 7,496,404 B2 | 2/2009 | Meadows et al. |
| 7,502,651 B2 | 3/2009 | Kim et al. |
| 7,515,965 B2 | 4/2009 | Gerber et al. |
| 7,515,967 B2 | 4/2009 | Phillips et al. |
| 7,522,953 B2 | 4/2009 | Kaula et al. |
| 7,532,936 B2 | 5/2009 | Erickson et al. |
| 7,539,538 B2 | 5/2009 | Parramon et al. |
| 7,551,958 B2 | 6/2009 | Libbus et al. |
| 7,551,960 B2 | 6/2009 | Forsberg et al. |
| 7,555,346 B1 | 6/2009 | Woods et al. |
| 7,555,347 B2 | 6/2009 | Loeb |
| 7,565,199 B2 | 7/2009 | Sheffield et al. |
| 7,565,203 B2 | 7/2009 | Greenberg et al. |
| 7,571,000 B2 | 8/2009 | Boggs, II et al. |
| 7,577,481 B2 | 8/2009 | Firlik et al. |
| 7,578,819 B2 | 8/2009 | Bleich et al. |
| 7,580,752 B2 | 8/2009 | Gerber et al. |
| 7,580,753 B2 | 8/2009 | Kim et al. |
| 7,582,053 B2 | 9/2009 | Gross et al. |
| 7,582,058 B1 | 9/2009 | Miles et al. |
| 7,613,516 B2 | 11/2009 | Cohen et al. |
| 7,617,002 B2 | 11/2009 | Goetz |
| 7,620,456 B2 | 11/2009 | Gliner et al. |
| 7,623,925 B2 | 11/2009 | Grill et al. |
| 7,636,602 B2 | 12/2009 | Baru Fassio et al. |
| 7,640,059 B2 | 12/2009 | Forsberg et al. |
| 7,643,880 B2 | 1/2010 | Tanagho et al. |
| 7,650,192 B2 | 1/2010 | Wahlstrand |
| 7,664,544 B2 | 2/2010 | Miles et al. |
| 7,672,730 B2 | 3/2010 | Firlik et al. |
| 7,706,889 B2 | 4/2010 | Gerber et al. |
| 7,720,547 B2 | 5/2010 | Denker et al. |
| 7,720,548 B2 | 5/2010 | King |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,756,584 B2 | 7/2010 | Sheffield et al. |
| 7,771,838 B1 | 8/2010 | He et al. |
| 7,774,069 B2 | 8/2010 | Olson et al. |
| 7,801,601 B2 | 9/2010 | Maschino et al. |
| 7,801,619 B2 | 9/2010 | Gerber et al. |
| 7,805,196 B2 | 9/2010 | Miesel et al. |
| 7,813,803 B2 | 10/2010 | Heruth et al. |
| 7,813,809 B2 | 10/2010 | Strother et al. |
| 7,819,909 B2 | 10/2010 | Goetz et al. |
| 7,826,901 B2 | 11/2010 | Lee et al. |
| 7,831,305 B2 | 11/2010 | Gliner |
| 7,848,818 B2 | 12/2010 | Barolat et al. |
| 7,853,322 B2 | 12/2010 | Bourget et al. |
| 7,878,207 B2 | 2/2011 | Goetz et al. |
| 7,890,176 B2 | 2/2011 | Jaax et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,945,330 B2 | 5/2011 | Gliner et al. |
| 7,952,349 B2 | 5/2011 | Huang et al. |
| 7,957,797 B2 | 6/2011 | Bourget et al. |
| 7,957,809 B2 | 6/2011 | Bourget et al. |
| 7,957,818 B2 | 6/2011 | Swoyer |
| 7,962,218 B2 | 6/2011 | Balzer et al. |
| 7,966,073 B2 | 6/2011 | Pless et al. |
| 7,979,119 B2 | 7/2011 | Kothandaraman et al. |
| 7,979,126 B2 | 7/2011 | Payne et al. |
| 7,981,144 B2 | 7/2011 | Geist et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,019,425 B2 | 9/2011 | Firlik et al. |
| 8,024,047 B2 | 9/2011 | Olson et al. |
| 8,027,716 B2 | 9/2011 | Gharib et al. |

(56) References Cited

U.S. PATENT DOCUMENTS

| | | |
|---|---|---|
| 8,036,756 B2 | 10/2011 | Swoyer et al. |
| 8,044,635 B2 | 10/2011 | Peterson |
| 8,050,753 B2 | 11/2011 | Libbus et al. |
| 8,050,767 B2 | 11/2011 | Sheffield et al. |
| 8,050,768 B2 | 11/2011 | Firlik et al. |
| 8,050,769 B2 | 11/2011 | Gharib et al. |
| 8,055,337 B2 | 11/2011 | Moffitt et al. |
| 8,055,349 B2 | 11/2011 | Gharib et al. |
| 8,065,012 B2 | 11/2011 | Firlik et al. |
| 8,068,912 B2 | 11/2011 | Kaula et al. |
| 8,073,546 B2 | 12/2011 | Sheffield et al. |
| 8,082,039 B2 | 12/2011 | Kim et al. |
| 8,083,663 B2 | 12/2011 | Gross et al. |
| 8,103,360 B2 | 1/2012 | Foster |
| 8,108,049 B2 | 1/2012 | King |
| 8,112,155 B2 | 2/2012 | Einav et al. |
| 8,116,862 B2 | 2/2012 | Stevenson et al. |
| 8,121,701 B2 | 2/2012 | Woods et al. |
| 8,121,702 B2 | 2/2012 | King |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,147,421 B2 | 4/2012 | Farquhar et al. |
| 8,150,530 B2 | 4/2012 | Wesselink |
| 8,155,753 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,182,423 B2 | 5/2012 | Miles et al. |
| 8,190,262 B2 | 5/2012 | Gerber et al. |
| 8,195,300 B2 | 6/2012 | Gliner et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,452 B2 | 7/2012 | Pless et al. |
| 8,224,460 B2 | 7/2012 | Schleicher et al. |
| 8,229,565 B2 | 7/2012 | Kim et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,326,433 B2 | 12/2012 | Blum et al. |
| 8,332,040 B1 | 12/2012 | Winstrom |
| 8,337,410 B2 | 12/2012 | Kelleher et al. |
| 8,340,786 B2 | 12/2012 | Gross et al. |
| 8,362,742 B2 | 1/2013 | Kallmyer |
| 8,369,943 B2 | 2/2013 | Shuros et al. |
| 8,380,314 B2 | 2/2013 | Panken et al. |
| 8,386,048 B2 | 2/2013 | McClure et al. |
| 8,391,972 B2 | 3/2013 | Libbus et al. |
| 8,396,555 B2 | 3/2013 | Boggs, II et al. |
| 8,412,335 B2 | 4/2013 | Gliner et al. |
| 8,417,346 B2 | 4/2013 | Giftakis et al. |
| 8,423,145 B2 | 4/2013 | Pless et al. |
| 8,423,146 B2 | 4/2013 | Giftakis et al. |
| 8,430,805 B2 | 4/2013 | Burnett et al. |
| 8,433,414 B2 | 4/2013 | Gliner et al. |
| 8,435,166 B2 | 5/2013 | Burnett et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,483,839 B2 | 7/2013 | Wesselink |
| 8,494,625 B2 | 7/2013 | Hargrove |
| 8,509,919 B2 | 8/2013 | Yoo et al. |
| 8,515,545 B2 | 8/2013 | Trier |
| 8,538,530 B1 | 9/2013 | Orinski |
| 8,543,223 B2 | 9/2013 | Sage et al. |
| 8,544,322 B2 | 10/2013 | Minami et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,634,904 B2 | 1/2014 | Kaula et al. |
| 8,634,932 B1 | 1/2014 | Ye et al. |
| 8,644,931 B2 | 2/2014 | Stadler et al. |
| 8,644,933 B2 | 2/2014 | Ozawa et al. |
| 8,655,451 B2 | 2/2014 | Klosterman et al. |
| 8,672,840 B2 | 3/2014 | Miles et al. |
| 8,694,115 B2 | 4/2014 | Goetz et al. |
| 8,700,175 B2 | 4/2014 | Fell |
| 8,706,254 B2 | 4/2014 | Vamos et al. |
| 8,712,546 B2 | 4/2014 | Kim et al. |
| 8,725,262 B2 | 5/2014 | Olson et al. |
| 8,725,269 B2 | 5/2014 | Nolan et al. |
| 8,731,656 B2 | 5/2014 | Bourget et al. |
| 8,738,141 B2 | 5/2014 | Smith et al. |
| 8,738,148 B2 | 5/2014 | Olson et al. |
| 8,740,783 B2 | 6/2014 | Gharib et al. |
| 8,744,585 B2 | 6/2014 | Gerber et al. |
| 8,750,985 B2 | 6/2014 | Parramon et al. |
| 8,761,897 B2 | 6/2014 | Kaula et al. |
| 8,768,450 B2 | 7/2014 | Gharib et al. |
| 8,768,452 B2 | 7/2014 | Gerber |
| 8,774,912 B2 | 7/2014 | Gerber |
| 8,805,518 B2 | 8/2014 | King et al. |
| 8,812,116 B2 | 8/2014 | Kaula et al. |
| 8,825,163 B2 | 9/2014 | Grill et al. |
| 8,825,175 B2 | 9/2014 | King |
| 8,831,731 B2 | 9/2014 | Blum et al. |
| 8,831,737 B2 | 9/2014 | Wesselink |
| 8,849,632 B2 | 9/2014 | Sparks et al. |
| 8,855,767 B2 | 10/2014 | Faltys et al. |
| 8,855,773 B2 | 10/2014 | Kokones et al. |
| 8,868,199 B2 | 10/2014 | Kaula et al. |
| 8,903,486 B2 | 12/2014 | Bourget et al. |
| 8,918,174 B2 | 12/2014 | Woods et al. |
| 8,918,184 B1 | 12/2014 | Torgerson et al. |
| 8,954,148 B2 | 2/2015 | Labbe et al. |
| 8,989,861 B2 | 3/2015 | Su et al. |
| 9,044,592 B2 | 6/2015 | Imran et al. |
| 9,050,473 B2 | 6/2015 | Woods et al. |
| 9,089,712 B2 | 7/2015 | Joshi et al. |
| 9,108,063 B2 | 8/2015 | Olson et al. |
| 9,144,680 B2 | 9/2015 | Kaula et al. |
| 9,149,635 B2 | 10/2015 | Denison et al. |
| 9,155,885 B2 | 10/2015 | Wei et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,320,899 B2 | 4/2016 | Parramon et al. |
| 9,333,339 B2 | 5/2016 | Weiner |

(56) References Cited

U.S. PATENT DOCUMENTS

| | | |
|---|---|---|
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,427,574 B2 | 8/2016 | Lee et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,555,246 B2 | 1/2017 | Jiang et al. |
| 9,561,372 B2 | 2/2017 | Jiang et al. |
| 9,592,389 B2 | 3/2017 | Moffitt |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,782,596 B2 | 10/2017 | Vamos et al. |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,849,278 B2 | 12/2017 | Spinelli et al. |
| 9,855,423 B2 | 1/2018 | Jiang et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,086,191 B2 | 10/2018 | Bonde et al. |
| 10,086,203 B2 | 10/2018 | Kaemmerer |
| 10,092,747 B2 | 10/2018 | Sharma et al. |
| 10,092,749 B2 | 10/2018 | Stevenson et al. |
| 10,092,762 B2 | 10/2018 | Jiang et al. |
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | LeBaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,406,369 B2 | 9/2019 | Jiang et al. |
| 10,448,889 B2 | 10/2019 | Gerber et al. |
| 10,456,574 B2 | 10/2019 | Chen et al. |
| 10,471,262 B2 | 11/2019 | Perryman et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 10,729,903 B2 | 8/2020 | Jiang et al. |
| 2002/0002390 A1 | 1/2002 | Fischell et al. |
| 2002/0010498 A1 | 1/2002 | Rigaux et al. |
| 2002/0010499 A1 | 1/2002 | Rigaux et al. |
| 2002/0040185 A1 | 4/2002 | Atalar et al. |
| 2002/0051550 A1 | 5/2002 | Leysieffer |

(56) References Cited

U.S. PATENT DOCUMENTS

| | | |
|---|---|---|
| 2002/0051551 A1 | 5/2002 | Leysieffer et al. |
| 2002/0055761 A1 | 5/2002 | Mann et al. |
| 2002/0077572 A1 | 6/2002 | Fang et al. |
| 2002/0140399 A1 | 10/2002 | Echarri et al. |
| 2002/0169485 A1 | 11/2002 | Pless et al. |
| 2002/0177884 A1 | 11/2002 | Ahn et al. |
| 2003/0114899 A1 | 6/2003 | Woods et al. |
| 2003/0120323 A1 | 6/2003 | Meadows et al. |
| 2003/0195586 A1 | 10/2003 | Rigaux et al. |
| 2003/0195587 A1 | 10/2003 | Rigaux et al. |
| 2003/0212440 A1 | 11/2003 | Boveja |
| 2004/0098068 A1 | 5/2004 | Carbunaru et al. |
| 2004/0158298 A1 | 8/2004 | Gliner et al. |
| 2004/0210290 A1 | 10/2004 | Omar-Pasha |
| 2004/0250820 A1 | 12/2004 | Forsell |
| 2004/0260357 A1 | 12/2004 | Vaughan et al. |
| 2004/0260358 A1 | 12/2004 | Vaughan et al. |
| 2004/0267137 A1 | 12/2004 | Peszynski et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0049648 A1 | 3/2005 | Cohen et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1 | 4/2005 | Olson et al. |
| 2005/0075698 A1 | 4/2005 | Phillips et al. |
| 2005/0075699 A1 | 4/2005 | Olson et al. |
| 2005/0075700 A1 | 4/2005 | Schommer et al. |
| 2005/0085743 A1 | 4/2005 | Hacker et al. |
| 2005/0104577 A1 | 5/2005 | Matei et al. |
| 2005/0119713 A1 | 6/2005 | Whitehurst et al. |
| 2005/0182454 A1 | 8/2005 | Gharib et al. |
| 2005/0187590 A1 | 8/2005 | Boveja et al. |
| 2005/0240238 A1 | 10/2005 | Mamo et al. |
| 2006/0009816 A1 | 1/2006 | Fang et al. |
| 2006/0142822 A1 | 6/2006 | Tulgar |
| 2006/0149345 A1 | 7/2006 | Boggs, II et al. |
| 2006/0200205 A1 | 9/2006 | Haller |
| 2006/0206166 A1 | 9/2006 | Weiner |
| 2007/0025675 A1 | 2/2007 | Kramer |
| 2007/0032834 A1 | 2/2007 | Gliner et al. |
| 2007/0032836 A1 | 2/2007 | Thrope et al. |
| 2007/0049988 A1 | 3/2007 | Carbunaru et al. |
| 2007/0054804 A1 | 3/2007 | Suty-Heinze |
| 2007/0100388 A1 | 5/2007 | Gerber |
| 2007/0208227 A1 | 9/2007 | Smith et al. |
| 2007/0239224 A1 | 10/2007 | Bennett et al. |
| 2007/0245316 A1 | 10/2007 | Bates et al. |
| 2007/0245318 A1 | 10/2007 | Goetz et al. |
| 2007/0265675 A1 | 11/2007 | Lund et al. |
| 2007/0293914 A1 | 12/2007 | Woods et al. |
| 2008/0027514 A1 | 1/2008 | DeMulling et al. |
| 2008/0065178 A1 | 3/2008 | Kelleher et al. |
| 2008/0065182 A1 | 3/2008 | Strother et al. |
| 2008/0071191 A1 | 3/2008 | Kelleher et al. |
| 2008/0081958 A1 | 4/2008 | Denison et al. |
| 2008/0132969 A1 | 6/2008 | Bennett et al. |
| 2008/0154335 A1 | 6/2008 | Thrope et al. |
| 2008/0161874 A1 | 7/2008 | Bennett et al. |
| 2008/0167694 A1 | 7/2008 | Bolea et al. |
| 2008/0177348 A1 | 7/2008 | Bolea et al. |
| 2008/0177365 A1 | 7/2008 | Bolea et al. |
| 2008/0183236 A1 | 7/2008 | Gerber |
| 2008/0215112 A1 | 9/2008 | Firlik et al. |
| 2008/0269740 A1 | 10/2008 | Bonde et al. |
| 2008/0306325 A1 | 12/2008 | Burnett et al. |
| 2009/0018617 A1 | 1/2009 | Skelton et al. |
| 2009/0036946 A1 | 2/2009 | Cohen et al. |
| 2009/0036951 A1 | 2/2009 | Heruth et al. |
| 2009/0048531 A1 | 2/2009 | McGinnis et al. |
| 2009/0054804 A1 | 2/2009 | Gharib et al. |
| 2009/0076565 A1 | 3/2009 | Surwit |
| 2009/0118788 A1 | 5/2009 | Firlik et al. |
| 2009/0157141 A1 | 6/2009 | Chiao et al. |
| 2009/0171381 A1 | 7/2009 | Schmitz et al. |
| 2009/0204176 A1 | 8/2009 | Miles et al. |
| 2009/0227829 A1 | 9/2009 | Burnett et al. |
| 2009/0281596 A1 | 11/2009 | King et al. |
| 2009/0287272 A1 | 11/2009 | Kokones et al. |
| 2009/0287273 A1 | 11/2009 | Carlton et al. |
| 2009/0306746 A1 | 12/2009 | Blischak |
| 2010/0023084 A1 | 1/2010 | Gunderson |
| 2010/0076254 A1 | 3/2010 | Jimenez et al. |
| 2010/0076534 A1 | 3/2010 | Mock |
| 2010/0100158 A1 | 4/2010 | Thrope et al. |
| 2010/0131030 A1 | 5/2010 | Firlik et al. |
| 2010/0145427 A1 | 6/2010 | Gliner et al. |
| 2010/0152808 A1 | 6/2010 | Boggs, II |
| 2010/0152809 A1 | 6/2010 | Boggs, II |
| 2010/0160712 A1 | 6/2010 | Burnett et al. |
| 2010/0168820 A1 | 7/2010 | Maniak et al. |
| 2010/0204538 A1 | 8/2010 | Burnett et al. |
| 2010/0222629 A1 | 9/2010 | Burnett et al. |
| 2010/0317989 A1 | 12/2010 | Gharib et al. |
| 2011/0004264 A1 | 1/2011 | Siejko et al. |
| 2011/0054562 A1 | 3/2011 | Gliner |
| 2011/0071593 A1 | 3/2011 | Parker et al. |
| 2011/0208263 A1 | 8/2011 | Balzer et al. |
| 2011/0238136 A1 | 9/2011 | Bourget et al. |
| 2011/0257701 A1 | 10/2011 | Strother et al. |
| 2011/0282416 A1 | 11/2011 | Hamann et al. |
| 2011/0301662 A1 | 12/2011 | Bar-Yoseph et al. |
| 2011/0301667 A1 | 12/2011 | Olson et al. |
| 2011/0313268 A1 | 12/2011 | Kokones et al. |
| 2012/0022611 A1 | 1/2012 | Firlik et al. |
| 2012/0029382 A1 | 2/2012 | Kelleher et al. |
| 2012/0041512 A1 | 2/2012 | Weiner |
| 2012/0046712 A1 | 2/2012 | Woods et al. |
| 2012/0101537 A1 | 4/2012 | Peterson et al. |
| 2012/0116741 A1 | 5/2012 | Choi et al. |
| 2012/0130448 A1 | 5/2012 | Woods et al. |
| 2012/0136413 A1 | 5/2012 | Bonde et al. |
| 2012/0165899 A1 | 6/2012 | Gliner |
| 2012/0197370 A1 | 8/2012 | Kim et al. |
| 2012/0238893 A1 | 9/2012 | Farquhar et al. |
| 2012/0253422 A1 | 10/2012 | Thacker et al. |
| 2012/0253442 A1 | 10/2012 | Gliner et al. |
| 2012/0265267 A1 | 10/2012 | Blum et al. |
| 2012/0271376 A1 | 10/2012 | Kokones et al. |
| 2012/0271382 A1 | 10/2012 | Arcot-Krishnamurthy et al. |
| 2012/0276854 A1 | 11/2012 | Joshi et al. |
| 2012/0276856 A1 | 11/2012 | Joshi et al. |
| 2012/0277621 A1 | 11/2012 | Gerber et al. |
| 2012/0277828 A1 | 11/2012 | O'Connor et al. |
| 2012/0277839 A1 | 11/2012 | Kramer et al. |
| 2012/0290055 A1 | 11/2012 | Boggs, II |
| 2012/0296395 A1 | 11/2012 | Hamann et al. |
| 2012/0310299 A1 | 12/2012 | Kaula et al. |
| 2012/0316630 A1 | 12/2012 | Firlik et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0041430 A1 | 2/2013 | Wang et al. |
| 2013/0072998 A1 | 3/2013 | Su et al. |
| 2013/0079840 A1 | 3/2013 | Su et al. |
| 2013/0120630 A1* | 5/2013 | Kim ............... H04N 5/232411 348/333.01 |
| 2013/0123568 A1 | 5/2013 | Hamilton et al. |
| 2013/0131755 A1 | 5/2013 | Panken et al. |
| 2013/0150925 A1 | 6/2013 | Vamos et al. |
| 2013/0165814 A1 | 6/2013 | Kaula et al. |
| 2013/0165991 A1 | 6/2013 | Kim et al. |
| 2013/0178758 A1 | 7/2013 | Kelleher et al. |
| 2013/0197608 A1 | 8/2013 | Eiger |
| 2013/0207863 A1 | 8/2013 | Joshi |
| 2013/0226261 A1 | 8/2013 | Sparks et al. |
| 2013/0245719 A1 | 9/2013 | Zhu et al. |
| 2013/0245722 A1 | 9/2013 | Temes et al. |
| 2013/0261684 A1 | 10/2013 | Howard |
| 2013/0289659 A1 | 10/2013 | Nelson et al. |
| 2013/0289664 A1 | 10/2013 | Johanek |
| 2013/0303828 A1 | 11/2013 | Hargrove |
| 2013/0310891 A1 | 11/2013 | Enrooth et al. |

(56) References Cited

U.S. PATENT DOCUMENTS

| | | |
|---|---|---|
| 2013/0310893 A1 | 11/2013 | Yoo et al. |
| 2013/0310894 A1 | 11/2013 | Trier |
| 2013/0331909 A1 | 12/2013 | Gerber |
| 2014/0062900 A1 | 3/2014 | Kaula et al. |
| 2014/0063003 A1 | 3/2014 | Kaula et al. |
| 2014/0063017 A1 | 3/2014 | Kaula et al. |
| 2014/0067006 A1 | 3/2014 | Kaula et al. |
| 2014/0067014 A1 | 3/2014 | Kaula et al. |
| 2014/0067016 A1 | 3/2014 | Kaula et al. |
| 2014/0067354 A1 | 3/2014 | Kaula et al. |
| 2014/0114385 A1 | 4/2014 | Nijhuis et al. |
| 2014/0142549 A1 | 5/2014 | Su et al. |
| 2014/0148870 A1 | 5/2014 | Burnett |
| 2014/0163579 A1 | 6/2014 | Tischendorf et al. |
| 2014/0163580 A1 | 6/2014 | Tischendorf et al. |
| 2014/0163644 A1 | 6/2014 | Scott et al. |
| 2014/0180363 A1 | 6/2014 | Zhu et al. |
| 2014/0194771 A1 | 7/2014 | Parker et al. |
| 2014/0194772 A1 | 7/2014 | Single et al. |
| 2014/0194942 A1 | 7/2014 | Sathaye et al. |
| 2014/0222112 A1 | 8/2014 | Fell |
| 2014/0235950 A1 | 8/2014 | Miles et al. |
| 2014/0236257 A1 | 8/2014 | Parker et al. |
| 2014/0237806 A1 | 8/2014 | Smith et al. |
| 2014/0243931 A1 | 8/2014 | Parker et al. |
| 2014/0249446 A1 | 9/2014 | Gharib et al. |
| 2014/0249599 A1 | 9/2014 | Kaula et al. |
| 2014/0277251 A1 | 9/2014 | Gerber et al. |
| 2014/0277270 A1 | 9/2014 | Parramon et al. |
| 2014/0288374 A1 | 9/2014 | Miles et al. |
| 2014/0288375 A1 | 9/2014 | Miles et al. |
| 2014/0288389 A1 | 9/2014 | Gharib et al. |
| 2014/0296737 A1 | 10/2014 | Parker et al. |
| 2014/0304773 A1 | 10/2014 | Woods et al. |
| 2014/0324144 A1 | 10/2014 | Ye et al. |
| 2014/0343628 A1 | 11/2014 | Kaula et al. |
| 2014/0343629 A1 | 11/2014 | Kaula et al. |
| 2014/0344733 A1 | 11/2014 | Kaula et al. |
| 2014/0344740 A1 | 11/2014 | Kaula et al. |
| 2014/0350636 A1 | 11/2014 | King et al. |
| 2015/0088227 A1 | 3/2015 | Shishilla et al. |
| 2015/0134027 A1 | 5/2015 | Kaula et al. |
| 2015/0214604 A1 | 7/2015 | Zhao et al. |
| 2015/0360030 A1 | 12/2015 | Cartledge et al. |
| 2016/0045724 A1 | 2/2016 | Lee et al. |
| 2016/0045745 A1 | 2/2016 | Mathur et al. |
| 2016/0045746 A1 | 2/2016 | Jiang et al. |
| 2016/0045747 A1 | 2/2016 | Jiang et al. |
| 2016/0045751 A1* | 2/2016 | Jiang ............ A61N 1/0551 607/59 |
| 2016/0114167 A1 | 4/2016 | Jiang et al. |
| 2016/0121123 A1 | 5/2016 | Jiang et al. |
| 2017/0189679 A1 | 7/2017 | Jiang et al. |
| 2017/0197079 A1 | 7/2017 | Illegems et al. |
| 2017/0209703 A1 | 7/2017 | Jiang et al. |
| 2017/0340878 A1 | 11/2017 | Wahlstrand et al. |
| 2018/0021587 A1 | 1/2018 | Strother et al. |
| 2018/0036477 A1 | 2/2018 | Olson et al. |
| 2019/0269918 A1 | 9/2019 | Parker |
| 2019/0351244 A1 | 11/2019 | Shishilla et al. |
| 2019/0358395 A1 | 11/2019 | Olson et al. |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CA | 2957967 | 11/2018 |
| CN | 101626804 | 1/2010 |
| CN | 101721200 | 6/2010 |
| CN | 102215909 | 10/2011 |
| CN | 103002947 | 3/2013 |
| CN | 102307618 | 3/2014 |
| CN | 107073258 | 2/2020 |
| DE | 3146182 | 6/1983 |
| EP | 0656218 | 6/1995 |
| EP | 1205004 | 5/2002 |
| EP | 1680182 | 7/2006 |
| EP | 1904153 | 4/2008 |
| EP | 2243509 | 10/2010 |
| EP | 1680182 | 5/2013 |
| EP | 1904153 | 4/2015 |
| EP | 3180072 | 11/2018 |
| ES | 2395128 | 2/2013 |
| HK | 1098715 | 3/2012 |
| JP | 2007505698 | 3/2007 |
| JP | 2007268293 | 10/2007 |
| JP | 4125357 | 7/2008 |
| JP | 2013500081 | 1/2013 |
| JP | 2013541381 | 11/2013 |
| JP | 6602371 | 11/2019 |
| WO | 9639932 | 12/1996 |
| WO | 9820933 | 5/1998 |
| WO | 9918879 | 4/1999 |
| WO | 9934870 | 7/1999 |
| WO | 9942173 | 8/1999 |
| WO | 0002623 | 1/2000 |
| WO | 0019939 | 4/2000 |
| WO | 0019940 | 4/2000 |
| WO | 0056677 | 9/2000 |
| WO | 0001320 | 11/2000 |
| WO | 0065682 | 11/2000 |
| WO | 0069012 | 11/2000 |
| WO | 0078389 | 12/2000 |
| WO | 0183029 | 11/2001 |
| WO | 0193759 | 12/2001 |
| WO | 0209808 | 2/2002 |
| WO | 0137728 | 8/2002 |
| WO | 02072194 | 9/2002 |
| WO | 02072194 | 3/2003 |
| WO | 02078592 | 3/2003 |
| WO | 03026739 | 4/2003 |
| WO | 03043690 | 5/2003 |
| WO | 03005887 | 8/2003 |
| WO | 03035163 | 9/2003 |
| WO | 03066162 | 3/2004 |
| WO | 2004021876 | 3/2004 |
| WO | 2004036765 | 4/2004 |
| WO | 03026482 | 5/2004 |
| WO | 2004047914 | 6/2004 |
| WO | 2004052448 | 6/2004 |
| WO | 2004052449 | 6/2004 |
| WO | 2004058347 | 7/2004 |
| WO | 2004064634 | 8/2004 |
| WO | 2004066820 | 8/2004 |
| WO | 2004087256 | 10/2004 |
| WO | 03037170 | 12/2004 |
| WO | 2004103465 | 12/2004 |
| WO | 2005000394 | 1/2005 |
| WO | 2005002664 | 3/2005 |
| WO | 2005002665 | 6/2005 |
| WO | 2005032332 | 8/2005 |
| WO | 2005079295 | 9/2005 |
| WO | 2005081740 | 9/2005 |
| WO | 2005105203 | 11/2005 |
| WO | 2005123185 | 12/2005 |
| WO | 2006012423 | 2/2006 |
| WO | 2006019764 | 2/2006 |
| WO | 2005081740 | 3/2006 |
| WO | 2006029257 | 3/2006 |
| WO | 2006091611 | 8/2006 |
| WO | 2006084194 | 10/2006 |
| WO | 2006116256 | 11/2006 |
| WO | 2006119015 | 11/2006 |
| WO | 2006119046 | 11/2006 |
| WO | 2006127366 | 11/2006 |
| WO | 2005087307 | 5/2007 |
| WO | 2007064924 | 6/2007 |
| WO | 2007064936 | 6/2007 |
| WO | 2007108863 | 9/2007 |
| WO | 2007089394 | 11/2007 |
| WO | 2008021524 | 2/2008 |
| WO | 2008039242 | 4/2008 |

(56) References Cited

FOREIGN PATENT DOCUMENTS

| | | |
|---|---|---|
| WO | 2008042902 | 8/2008 |
| WO | 2009021080 | 2/2009 |
| WO | 2009042379 | 4/2009 |
| WO | 2009051965 | 4/2009 |
| WO | 2009042172 | 7/2009 |
| WO | 2009134478 | 11/2009 |
| WO | 2009137119 | 11/2009 |
| WO | 2009139907 | 11/2009 |
| WO | 2009139909 | 11/2009 |
| WO | 2009139910 | 11/2009 |
| WO | 2010014055 | 2/2010 |
| WO | 2010014260 | 2/2010 |
| WO | 2009139917 | 3/2010 |
| WO | 2010065143 | 6/2010 |
| WO | 2011011748 | 1/2011 |
| WO | 2011053607 | 5/2011 |
| WO | 2011053661 | 5/2011 |
| WO | 2011059565 | 5/2011 |
| WO | 2011100162 | 8/2011 |
| WO | 2011139779 | 11/2011 |
| WO | 2011153024 | 12/2011 |
| WO | 2012054183 | 4/2012 |
| WO | 2011156286 | 5/2012 |
| WO | 2011156287 | 6/2012 |
| WO | 2012075265 | 6/2012 |
| WO | 2012075281 | 6/2012 |
| WO | 2012075299 | 6/2012 |
| WO | 2012075497 | 6/2012 |
| WO | 2012135733 | 10/2012 |
| WO | 2012155183 | 11/2012 |
| WO | 2012155184 | 11/2012 |
| WO | 2012155185 | 11/2012 |
| WO | 2012155186 | 11/2012 |
| WO | 2012155187 | 11/2012 |
| WO | 2012155188 | 11/2012 |
| WO | 2012155189 | 11/2012 |
| WO | 2012155190 | 11/2012 |
| WO | 2012158766 | 11/2012 |
| WO | 2013028428 | 2/2013 |
| WO | 2013036630 | 3/2013 |
| WO | 2013141996 | 9/2013 |
| WO | 2013155117 | 10/2013 |
| WO | 2013165395 | 11/2013 |
| WO | 2014035733 | 3/2014 |
| WO | 2012003451 | 4/2014 |
| WO | 2014089390 | 6/2014 |
| WO | 2014089392 | 6/2014 |
| WO | 2014089400 | 6/2014 |
| WO | 2014089405 | 6/2014 |
| WO | 2014089485 | 6/2014 |
| WO | 2013162708 | 7/2014 |
| WO | 2014161000 | 10/2014 |
| WO | 2014172381 | 10/2014 |

OTHER PUBLICATIONS

Bu-802a: How Does Rising Internal Resistance Affect Performance? Understanding the Importance of Low Conductivity, Battery University, Available Online at: https://batteryuniversity.com/learn/article/rising_internal_resistance, Accessed from Internet on May 15, 2020, 10 pages.

DOE Handbook: Primer on Lead-Acid Storage Batteries, United States Department of Energy, Available Online at: htt12s://www.stan dards.doe.gov/standards- documents/ 1 000/1084-bhdbk-1995/@@images/file, Sep. 1995, 54 pages.

Medical Electrical Equipment—Part 1: General Requirements for Safety, British Standard, BS EN 60601-1:1990-BS5724-1:1989, Mar. 1979, 200 pages.

Summary of Safety and Effectiveness, Medtronic InterStim System for Urinary Control, Apr. 15, 1999, pp. 1-18.

The Advanced Bionics PRECISION™ Spinal Cord Stimulator System, Advanced Bionics Corporation, Apr. 27, 2004, pp. 1-18.

UL Standard for Safety for Medical and Dental Equipment, Underwriters Laboratories 544, 4th edition, Dec. 30, 1998, 128 pages.

Barnhart et al., "A Fixed-Rate Rechargeable Cardiac Pacemaker", Applied Physics Laboratory Technical Digest, Jan.-Feb. 1970, pp. 2-9.

Benditt et al., "A Combined Atrial/Ventricular Lead for Permanent Dual-Chamber Cardiac Pacing Applications", Chest, vol. 83, No. 6, Jun. 1983, pp. 929-931.

Bosch et al., "Sacral (S3) Segmental Nerve Stimulation as a Treatment for Urge Incontinence in Patients with Detrusor Instability: Results of Chronic Electrical Stimulation Using an Implantable Neural Prosthesis", The Journal of Urology, vol. 154, No. 2, Aug. 1995, pp. 504-507.

Boyce et al., "Research Related to the Development of an Artificial Electrical Stimulator for the Paralyzed Human Bladder: A Review", The Journal of Urology, vol. 91, No. 1, Jan. 1964, pp. 41-51.

Bradley et al., "Further Experience with the Radio Transmitter Receiver Unit for the Neurogenic Bladder", Journal of Neurosurgery, vol. 20, No. 11, Nov. 1963, pp. 953-960.

Broggi et al., "Electrical Stimulation of the Gasserian Ganglion for Facial Pain: Preliminary Results", Acta Neurochirurgica, vol. 39, 1987, pp. 144-146.

Buhlmann et al., "Modeling of a Segmented Electrode for Desynchronizing Deep Brain Stimulation", Frontiers in Neuroengineering, vol. 4, No. 15, Dec. 8, 2011, 8 pages.

Cameron et al., "Effects of Posture on Stimulation Parameters in Spinal Cord Stimulation", Neuromodulation, vol. 1, No. 4, Oct. 1998, pp. 177-183.

Connelly et al., "Atrial Pacing Leads Following Open Heart Surgery: Active or Passive Fixation?", Pacing and Clinical Electrophysiology, vol. 20, No. 10, Oct. 1997, pp. 2429-2433.

Fischell, "The Development of Implantable Medical Devices at the Applied Physics Laboratory", Johns Hopkins Applied Physics Laboratory Technical Digest, vol. 13 No. 1, 1992, pp. 233-243.

Gaunt et al., "Control of Urinary Bladder Function with Devices: Successes and Failures", Progress in Brain Research, vol. 152, 2006, pp. 1-24.

Ghovanloo et al., "A Small Size Large Voltage Compliance Programmable Current Source for Biomedical Implantable Microstimulators", Proceedings of the 25th Annual International Conference of the Institute of Electrical and Electronics Engineers, Engineering in Medicine and Biology Society, Sep. 17-21, 2003, pp. 1979-1982.

Hansen et al., "Urethral Sphincter Emg as Event Detector For Neurogenic Detrusor Overactivity", IEEE Transactions on Biomedical Engineering, vol. 54, No. 7, Jul. 31, 2007, pp. 1212-1219.

Helland, "Technical Improvements to be Achieved by the Year 2000: Leads and Connector Technology", Rate Adaptive Cardiac Pacing, Springer Verlag, 1993, pp. 279-292.

Hidefjall, "The Pace of Innovation—Patterns of Innovation in the Cardiac Pacemaker Industry", Linkoping University Press, 1997, 398 pages.

Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.

Jonas et al., "Studies on the Feasibility of Urinary Bladder Evacuation by Direct Spinal Cord Stimulation. I. Parameters of Most Effective Stimulation", Investigative Urology, vol. 13, No. 2, 1975, pp. 142-150.

Kakuta et al., "In Vivo Long Term Evaluation of Transcutaneous Energy Transmission for Totally Implantable Artificial Heart", American Society for Artificial Internal Organs Journal, Mar.-Apr. 2000, pp. 1-2.

Kester et al., "Voltage-to-Frequency Converters", Available Online at: https://www.analog.com/media/cn/training-seminars/tutorials/MT-028.pdf, 7 pages.

Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.

Lewis et al., "Early Clinical Experience with the Rechargeable Cardiac Pacemaker", The Annals of Thoracic Surgery, vol. 18, No. 5, Nov. 1974, pp. 490-493.

(56) References Cited

OTHER PUBLICATIONS

Love et al., "Experimental Testing of a Permanent Rechargeable Cardiac Pacemaker", The Annals of Thoracic Surgery, vol. 17, No. 2, Feb. 1, 1974, pp. 152-156.
Love, "Pacemaker Troubleshooting and Follow-up", Clinical Cardiac Pacing, Defibrillation, and Resynchronization Therapy, Chapter 24, 2007, pp. 1005-1062.
Madigan et al., "Difficulty of Extraction of Chronically Implanted Tined Ventricular Endocardial Leads", Journal of the American College of Cardiology, vol. 3, No. 3, Mar. 1984, pp. 724-731.
McLennan, "The Role of Electrodiagnostic Techniques in the Reprogramming of Patients with a Delayed Suboptimal Response to Sacral Nerve Stimulation", International Urogynecology Journal, vol. 14, No. 2, Jun. 2003, pp. 98-103.
Meglio, "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.
Meyerson, "Alleviation of Atypical Trigeminal Pain by Stimulation of the Gasserian Ganglion via an Implanted Electrode", Acta Neurochirurgica Suppiementum, vol. 30, 1980, pp. 303-309.
Mingming, "Development of an Implantable Epidural Spinal Cord Stimulator With Emg Biofeedback", China Master's Theses Fulltext Database: Engineering Technology, vol. 2, No. 6, May 23, 2013, 64 pages.
Mitamura et al., "Development of Transcutaneous Energy Transmission System", Available Online at https://www.researchgate.net/publication/312810915 Ch. 28, Jan. 1988, pp. 265-270.
Nakamura et al., "Biocompatibility and Practicality Evaluations of Transcutaneous Energy Transmission Unit for the Totally Implantable Artificial Heart System", Journal of Artificial Organs, vol. 27, No. 2, 1998, pp. 347-351.
Nashold et al., "Electromicturition in Paraplegia. Implantation of a Spinal Neuroprosthesis", Archives of Surgery., vol. 104, Feb. 1972, pp. 195-202.
Noblett, "Neuromodulation and the Role of Electrodiagnostic Techniques", International Urogynecology Journal, vol. 21, No. 2, Dec. 2010, 13 pages.
Painter et al., "Implantation of an Endocardial Tined Lead to Prevent Early Dislodgement", The Journal of Thoracic and Cardiovascular Surgery, vol. 77, No. 2, Feb. 1979, pp. 249-251.
Perez, "Lead-Acid Battery State of Charge vs. Voltage", Available Online at http://www.rencobattery.com/resources/SOC vs-Voltage.pdf, Aug.-Sep. 1993, 5 pages.
Schaldach et al., "A Long-Lived, Reliable, Rechargeable Cardiac Pacemaker", Engineering in Medicine, vol. 1: Advances in Pacemaker Technology, 1975, 34 pages.
Scheuer-Leeser et al., "Polyurethane Leads: Facts and Controversy", PACE, vol. 6, Mar.-Apr. 1983, pp. 454-458.
Smith, "Changing Standards for Medical Equipment", UL 544 and UL 187 vs. UL 2601 ("Smith"), 2002, 8 pages.
Tanagho et al., "Bladder Pacemaker: Scientific Basis and Clinical Future", Urology, vol. 20, No. 6, Dec. 1982, pp. 614-619.
Tanagho, "Neuromodulation and Neurostimulation: Overview and Future Potential", Translational Androl Urol, vol. 1, No. 1, 2012, pp. 44-49.
Torres et al., "Electrostatic Energy-Harvesting and Battery-Charging CMOS System Prototype", IEEE Transactions on Circuits and Systems I: Regular Papers, vol. 56, No. 9, Dec. 22, 2008, pp. 1938-1948.
Young, "Electrical Stimulation of the Trigeminal Nerve Root for the Treatment of Chronic Facial Pain", Journal of Neurosurgery, vol. 83, No. 1, Jul. 1995, pp. 72-78.
U.S. Appl. No. 14/827,067, filed Aug. 14, 2015.
U.S. Appl. No. 14/827,074, filed Aug. 14, 2015.
U.S. Appl. No. 14/827,081, filed Aug. 14, 2015.
U.S. Appl. No. 14/827,095, filed Aug. 14, 2015.
U.S. Appl. No. 14/827,108, filed Aug. 14, 2015.
U.S. Appl. No. 14/991,649, filed Jan. 8, 2016.
U.S. Appl. No. 14/991,752, filed Jan. 8, 2016.
U.S. Appl. No. 14/991,784, filed Jan. 8, 2016.
U.S. Appl. No. 62/038,122, filed Aug. 15, 2014.
U.S. Appl. No. 62/101,666, filed Jan. 9, 2015.
U.S. Appl. No. 62/101,782, filed Jan. 9, 2015.
U.S. Appl. No. 62/101,884, filed Jan. 9, 2015.
U.S. Appl. No. 62/101,888, filed Jan. 9, 2015.
U.S. Appl. No. 62/101,897, filed Jan. 9, 2015.
U.S. Appl. No. 62/101,899, filed Jan. 9, 2015.
U.S. Appl. No. 62/110,274, filed Jan. 30, 2015.
U.S. Appl. No. 62/191,134, filed Jul. 10, 2015.

* cited by examiner

CLINICIAN PROGRAMMER METHODS AND SYSTEMS FOR MAINTAINING TARGET OPERATING TEMPERATURES

CROSS-REFERENCE TO RELATED APPLICATIONS

This application claims the benefit of U.S. Provisional Application No. 62/852,805 filed May 24, 2019, and entitled "CLINICIAN PROGRAMMER METHODS AND SYSTEMS FOR MAINTAINING TARGET OPERATING TEMPERATURES", the entirety of which is hereby incorporated by reference herein.

FIELD OF THE INVENTION

The present invention relates to neurostimulation treatment systems and associated devices, as well as methods of monitoring and regulating these systems and associated devices.

BACKGROUND OF THE INVENTION

Treatments with neurostimulation systems have become increasingly common in recent years. These neurostimulation systems generally have a neurostimulation component (for example, a pulse generator) and one or more interfacing components. The pulse generator may be an implantable pulse generator (IPG) or an external pulse generator (EPG). The interfacing components may include a neurostimulator programmer, which may be a clinician programmer (CP) or a patient remote for example. The neurostimulator programmer may be able to, for example, adjust stimulation parameters, turn stimulation on or off, receive stimulation history from the pulse generator, and/or transmit programming instructions to the pulse generator.

While neurostimulation systems have been widely implemented in treating a number of conditions, there are still a number of implementation problems that need to be addressed. For example, neurostimulation programmers may operate non-optimally or may pose safety risks when they are subjected to excessive temperatures that may result from a combination of the environment in which they are used and heat produced by the neurostimulation programmers themselves. Thus, it may be advantageous to devise methods, systems, and devices for monitoring and regulating temperatures of neurostimulation programmers while they are in use so as to ensure optimal safety and efficacy. Given the effects of neurostimulation systems on patient health and the attending safety risks associated with these systems, it may be particularly desirable to monitor and regulate these systems.

BRIEF SUMMARY OF THE INVENTION

The present invention generally relates to neurostimulation treatment systems and associated devices and methods, and in particular to methods of monitoring and regulating temperatures of neurostimulation programmers. The present invention has particular application to sacral nerve stimulation treatment systems configured to treat bladder and bowel related dysfunctions. It will be appreciated however that the present invention may also be utilized for the treatment of pain, or other suitable indications, such as movement or affective disorders, as will be appreciated by one of skill in the art.

In some embodiments, the temperature of neurostimulator programmers may need to be monitored and/or regulated to abide by prescribed standards set by the manufacturer or by the regulating agency. For example, neurostimulator programmers may need to abide by safety and/or efficacy regulations that prescribe maximum temperatures or optimal temperatures that may be sustained by a neurostimulator programmer while it is in use. A neurostimulator programmer may include components that generate heat, and this heat may accumulate within the neurostimulator programmer such that it may exceed thresholds beyond which the neurostimulator programmer may not operate safely, or beyond which the neurostimulator programmer may not operate optimally. Moreover, in some instances, the environment in which the neurostimulator programmer may be operated may introduce heat. It is therefore advantageous for the neurostimulator programmer to make use of one or more temperature monitoring and/or regulating software algorithms to maintain safety and efficacy.

An Example First Temperature-Regulation Software

In some embodiments, a neurostimulator programmer may be configured to execute a first temperature-regulation software. In one aspect, methods in accordance with the present invention may include receiving a first temperature information from one or more sensors associated with a neurostimulator programmer. The first temperature information may include one or more first temperature values. Each of the first temperature values may be associated with a particular one of the sensors. The method may include determining that one of the first temperature values exceeds a respective sensor-specific threshold value, wherein the respective sensor-specific threshold value corresponds to the respective sensor associated with the one of the first temperature values. In response to determining that the one of the first temperature values exceeds its respective sensor-specific threshold value, the method may include reducing a charge rate of a charger module of the neurostimulator programmer to a reduced charge rate. For example, the reduced charge rate may be 25% of the maximum charge rate. The method may include receiving a second temperature information from one or more of the sensors so as to continue temperature monitoring of the neurostimulator programmer, wherein the second temperature information may include one or more second temperature values. Each of the second temperature values may be associated with a particular one of the sensors. In one aspect, the second temperature information may be received after a predetermined first period of time (for example, about 1 minute) elapses after reducing the charge rate of charger module.

In one aspect, the one or more sensors may include a display sensor disposed within a housing of the neurostimulator programmer, the display sensor being disposed near an inverter that powers a display of the neurostimulator programmer. As an example, the inverter may be a cold-cathode fluorescent lamp (CCFL) backlight inverter, and the display may be an LCD display. The respective sensor-specific threshold value corresponding to the display sensor may be any suitable value (for example, about 45 degrees Celsius). In one aspect, the one or more sensors may include a charger sensor disposed near the charger module of the neurostimulator programmer. The respective sensor-specific threshold value corresponding to the display sensor may be any suitable value (for example, about 42 degrees Celsius). In one aspect, the first temperature information may include a first temperature value associated with a first sensor disposed near an inverter that powers a display of the neurostimulator programmer, and a first temperature value associated with a second sensor disposed at a different location. As an example, the second sensor may be disposed near the charger module of the neurostimulator. In one aspect, any suitable sensor may be used in generating the first temperature information. For example, the first temperature information may include a first temperature value associated with a sensor disposed near a CPU of the neurostimulator programmer. As another example, the first temperature information may include a first temperature value associated with a sensor disposed near a battery of the neurostimulator programmer. In one aspect, the first temperature information may include temperature values from the same set of sensors as the second temperature information.

In one aspect, the neurostimulator programmer may adjust functionality of any other suitable heat-generating component. For example, it may adjust a clock speed of the CPU (for example, based on the first temperature value exceeding a sensor-specific threshold value).

In one aspect, the neurostimulator programmer may determine that each of the second temperature values is at or below a respective sensor-specific threshold value. Each respective sensor-specific threshold value may correspond to the respective sensor associated with one of the second temperature values. In response to determining that each of the second temperature values is at or below its respective sensor-specific threshold value, the neurostimulator programmer may increase the charge rate by a predetermined amount. It may initiate a follow-up process that may include: (a) waiting for a predetermined period of time; (b) receiving a follow-up temperature information from one or more of the sensors after waiting for the predetermined period of time, wherein the follow-up temperature information comprises one or more follow-up temperature values; (c) determining that each of the follow-up temperature values is below its respective sensor-specific threshold value; (d) increasing the charge rate by the predetermined amount; and (e) repeating steps (a)-(d) until the charge rate reaches a maximum charge rate or until one of the follow-up temperature values exceeds its respective sensor-specific threshold value.

In one aspect, the neurostimulator programmer may determine that one of the second temperature values exceeds a respective sensor-specific threshold value. The respective sensor-specific threshold value may correspond to the respective sensor associated with the one of the second temperature values. In response to determining that the one of the second temperature values exceeds its respective sensor-specific threshold value, the neurostimulator programmer may reduce a brightness level of a display of the neurostimulator programmer by a predetermined brightness-reduction amount (for example, 10% of a maximum brightness level). In one aspect, after reducing the brightness level of the display in response to determining that the one of the second temperature values exceeds its respective sensor-specific threshold value, the neurostimulator programmer may (a) wait for a predetermined first period of time; (b) receive a subsequent temperature information from one or more of the sensors after waiting for the predetermined first period of time, wherein the subsequent temperature information may include one or more subsequent temperature values; (c) determine that one of the subsequent temperature values exceeds a respective sensor-specific threshold value; (d) in response to determining that the one of the subsequent temperature values exceeds its respective sensor-specific threshold value, reduce the brightness level of a display of the neurostimulator programmer by the predetermined brightness-reduction amount; and (e) repeat steps (a)-(d) until the brightness level of the display reaches a minimum brightness level or until each of the subsequent temperature values is at or below its respective sensor-specific threshold value.

In one aspect, in response to determining that the brightness level of the display has reached the minimum brightness level, initiating a continuous monitoring process. The continuous monitoring process may include the steps of: (a) waiting for a predetermined second period of time, wherein the predetermined second period of time may be less than the predetermined first period of time; (b) receiving a follow-up temperature information from one or more of the sensors after waiting for the predetermined second period of time (for example, about 10 seconds), wherein the follow-up temperature information may include one or more follow-up temperature values; and (c) repeating steps (a)-(b) until each of the follow-up temperature values is at or below its respective sensor-specific threshold values.

In one aspect, the neurostimulator programmer may (a) receive a third temperature information from one or more of the sensors comprising one or more third temperature values; (b) determine that each of the third temperature values is at or below a respective sensor-specific nominal value (for example, about 42 degrees Celsius as measured by a sensor disposed near an inverter that powers a display of the neurostimulator programmer); (c) in response to determining that each of the third temperature values is at or below its respective sensor-specific nominal value, increase the brightness level of the display by a predetermined brightness-increase amount; (d) wait for a predetermined third period of time (for example, about 1 minute) after increasing the brightness level of the display; and (e) repeat steps (a)-(d) until the brightness level of the display reaches a user-set level. In one aspect, the brightness-increase amount may be the same as the brightness-reduction amount. In one aspect, the neurostimulator programmer may increase the charge rate of the charger module (for example, to a maximum charge rate, or incrementally by a predetermined amount) after the brightness level of the display reaches the user-set level.

An Example Second Temperature-Regulation Software

In some embodiments, the neurostimulator programmer may be configured to execute a second temperature-regulation software (for example, for handling particularly excessive temperatures). In one aspect, the neurostimulator programmer may receive a first temperature information from one or more sensors associated with the neurostimulator programmer, wherein the first temperature information may include one or more first temperature values. Each of the first temperature values may be associated with a particular one of the sensors. The neurostimulator programmer may determine that one of the first temperature values exceeds a respective sensor-specific high-threshold value, wherein the respective sensor-specific high-threshold value may correspond to the respective sensor associated with the one of the first temperature values. In particular embodiments, each respective sensor-specific high-threshold value may indicate an unsafe operating temperature. In particular embodiments, the sensor-specific high-threshold values of the second temperature-regulation software may be higher temperature values than the corresponding sensor-specific threshold values of the first temperature-regulation software. In response to determining that the one of the first temperature values exceeds its respective sensor-specific high-threshold value, the neurostimulator programmer may initiate a process that may include: (a) waiting for a predetermined first period of time; (b) after waiting for the predetermined first period of time, receiving a second temperature information from one or more of the sensors, the second temperature information comprising one or more second temperature values; (c) determining whether one of the second temperature values exceeds a respective sensor-specific high-threshold value; and (d) repeating steps (a)-(c) for a predetermined maximum number of times (for example, 5 times) or until each of the second temperature values is at or below its respective sensor-specific high-threshold value. In one aspect, the neurostimulator programmer may determine that steps (a)-(c) have been repeated consecutively for the predetermined maximum number of times, and may cause the neurostimulator programmer to initiate a shutdown of the neurostimulation programmer. Alternatively, the neurostimulator programmer may determine that each of the second temperature values is at or below its respective sensor-specific high-threshold value. It may initiate a monitoring process, which may include the steps of: waiting for a predetermined second period of time; after waiting for the predetermined second period of time, receiving a third temperature information from one or more of the sensors, the third temperature information comprising one or more third temperature values; and determining whether one or more of the third temperature values exceeds a respective sensor-specific high-threshold value.

In one aspect, the predetermined first period of time may be less than the predetermined second period of time. As an example, the predetermined first period of time may be about 10 seconds. The predetermined second period of time may be about 1 minute.

In one aspect, in response to determining that the one of the first temperature values exceeds its respective sensor-specific high-threshold value, the neurostimulator programmer may initialize a counter, increment a counter, and determine whether the counter has been incremented to a maximum count, wherein the maximum count may correspond to the predetermined maximum number of times. In another aspect, the neurostimulator programmer may initialize a counter to have a value corresponding to the predetermined maximum number of times, decrement the counter, and determine whether the counter has been documented to a minimum count (for example, 0).

In one aspect, the one or more sensors may include a display sensor disposed within a housing of the neurostimulator programmer, the display sensor being disposed near an inverter that powers a display of the neurostimulator programmer. As an example, the inverter may be a CCFL backlight inverter, and the display may be an LCD display. The respective sensor-specific high-threshold value corresponding to the display sensor may be any suitable value (for example, about 50 degrees Celsius). In one aspect, the one or more sensors may include a charger sensor disposed near the charger module of the neurostimulator programmer, with a respective sensor-specific high-threshold value of a suitable value (for example, about 55 degrees Celsius). In one aspect, the one or more sensors may include a sensor disposed near a CPU of the neurostimulator programmer, with a respective sensor-specific high-threshold value of a suitable value (for example, about 90 degrees Celsius). In one aspect, the one or more sensors may include a sensor disposed near a battery of the neurostimulator programmer, with a respective sensor-specific high-threshold value of a suitable value (for example, about 45 degrees Celsius). In one aspect, the first temperature information may include a first temperature value associated with a first sensor disposed near an inverter that powers a display of the neurostimulator programmer, and a first temperature value associated with a second sensor disposed at a different location. As an example, the second sensor may be disposed near the charger module of the neurostimulator. In one aspect, any suitable sensor may be used in generating the first temperature information. In one aspect, the first temperature information may include temperature values from the same set of sensors as the second temperature information.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Figure 1:
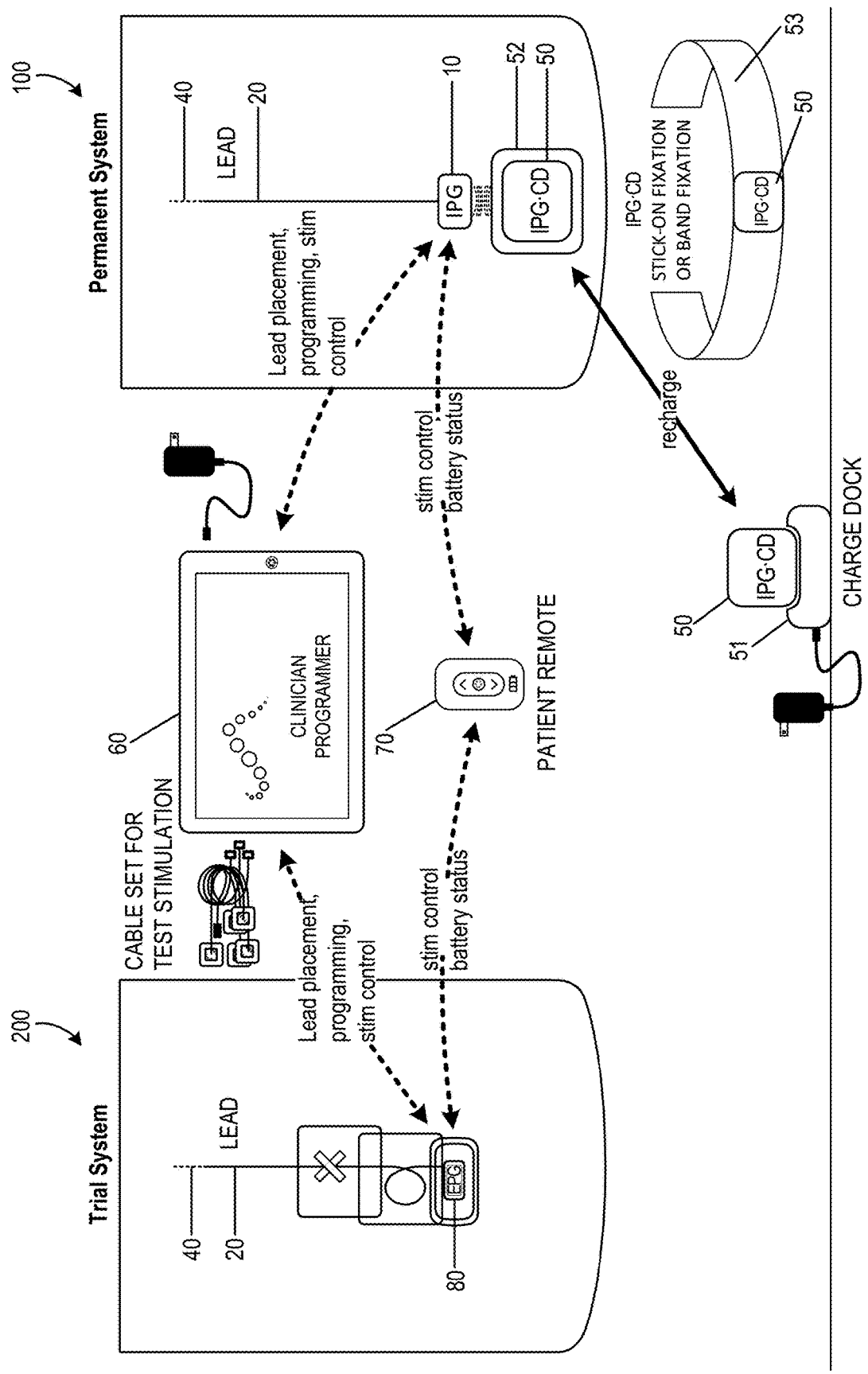
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment and configuration of such treatment systems. In particular embodiments, the invention relates to sacral nerve stimulation treatment systems configured to treat bladder dysfunctions, including overactive bladder ("OAB"), as well as fecal dysfunctions and relieve symptoms associated therewith. It will be appreciated however that the present invention may also be utilized for any variety of neuromodulation uses, such as fecal dysfunction, the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction and fecal dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 40 million Americans suffer from OAB. Of the adult population, about 16% of all men and women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of botulinum toxin (BTX), Percutaneous Tibial Nerve Stimulation (PTNS) and Sacral Nerve Stimulation (SNM). BTX is administered via a series of intradetrusor injections under cystoscopic guidance, but repeat injections of BTX are generally required every 4 to 12 months to maintain effect and BTX may undesirably result in urinary retention. A number or randomized controlled studies have shown some efficacy of BTX injections in OAB patients, but long-term safety and effectiveness of BTX for OAB is largely unknown.

PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, there is limited data on PTNS effectiveness beyond 3-years and PTNS is not recommended for patients seeking a cure for urge urinary incontinence (UUI) (e.g., 100% reduction in incontinence episodes) (EAU Guidelines).

II. Sacral Neuromodulation Overview

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

III. Example Systems

FIG. 1 schematically illustrates example nerve stimulation system setups, which includes a setup for use in a trial neurostimulation system 200 and a setup for use in a permanently implanted neurostimulation system 100, in accordance with aspects of the invention. The EPG 80 and IPG 50 are each compatible with and wirelessly communicate with a clinician programmer (CP) 60 and a patient remote 70, which are used in positioning and/or programming the trial neurostimulation system 200 and/or permanently implanted system 100 after a successful trial. As discussed above, the system utilizes a cable set and EMG sensor patches in the trial system setup 100 to facilitate lead placement and neurostimulation programming. CP can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the CP 60 is used by a physician to adjust the settings of the EPG and/or IPG while the lead is implanted within the patient. The CP can be a tablet computer used by the clinician to program the IPG, or to control the EPG during the trial period. The CP can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the CP 60 has a control unit which can include a microprocessor and specialized computer-code instructions for implementing methods and systems for use by a physician in deploying the treatment system and setting up treatment parameters. The CP generally includes a graphical user interface, an EMG module, an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the CP may be configured for coupling with an electrical ground or ground patch, an electrical pulse generator (e.g., an EPG or an IPG), or the like. As noted above, the CP can include a module with hardware and computer-code to execute EMG analysis, where the module can be a component of the control unit microprocessor, a pre-processing unit coupled to or in-line with the stimulation and/or sensory cables, or the like.

In other aspects, the CP 60 allows the clinician to read the impedance of each electrode contact whenever the lead is connected to an EPG, an IPG or a CP to ensure reliable connection is made and the lead is intact. This may be used as an initial step in both positioning the lead and in programming the leads to ensure the electrodes are properly functioning. The CP 60 is also able to save and display previous (e.g., up to the last four) programs that were used by a patient to help facilitate re-programming. In some embodiments, the CP 60 further includes a USB port for saving reports to a USB drive and a charging port. The CP is configured to operate in combination with an EPG when placing leads in a patient body as well with the IPG during programming. The CP can be electronically coupled to the EPG during test simulation through a specialized cable set or through wireless communication, thereby allowing the CP to configure, modify, or otherwise program the electrodes on the leads connected to the EPG. The CP may also include physical on/off buttons to turn the CP on and off and/or to turn stimulation on and off.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2:
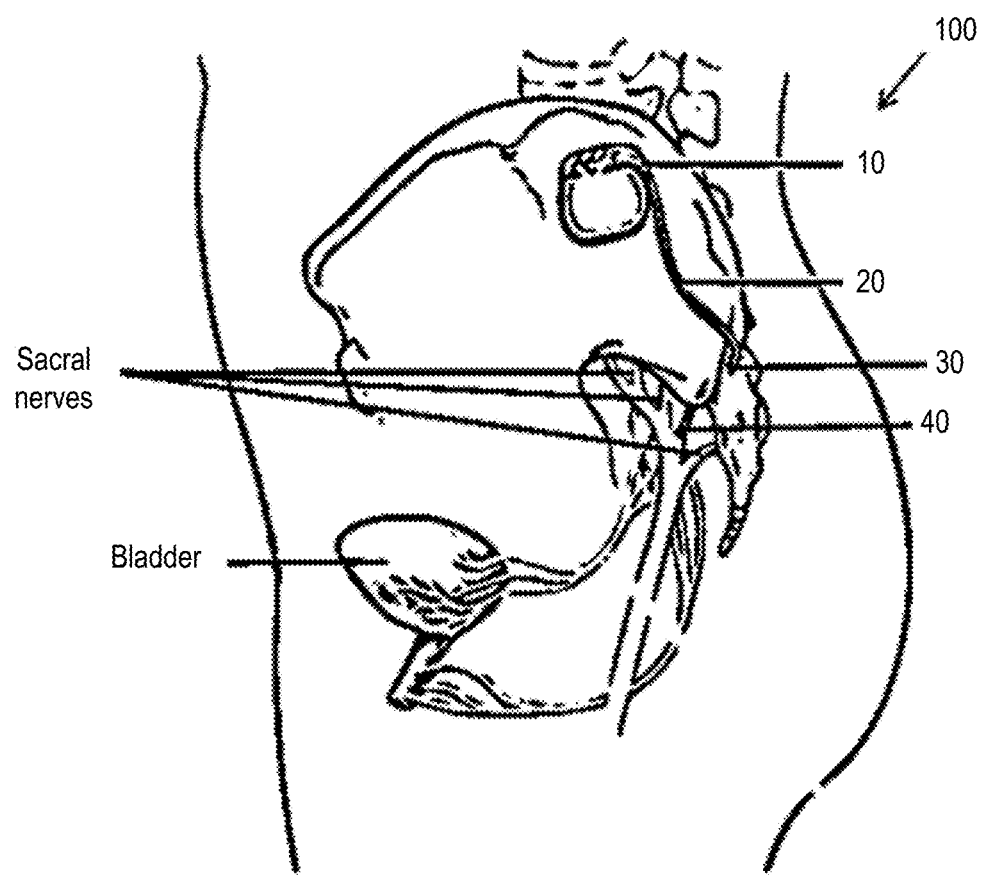
FIG. 2 illustrates an example of a fully implanted neurostimulation system in accordance with aspects of the invention.

FIG. 2 schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, amplitude, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 2, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

In one aspect, the EPG unit is wirelessly controlled by a patient remote and/or the CP in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The CP can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

Figure 3:
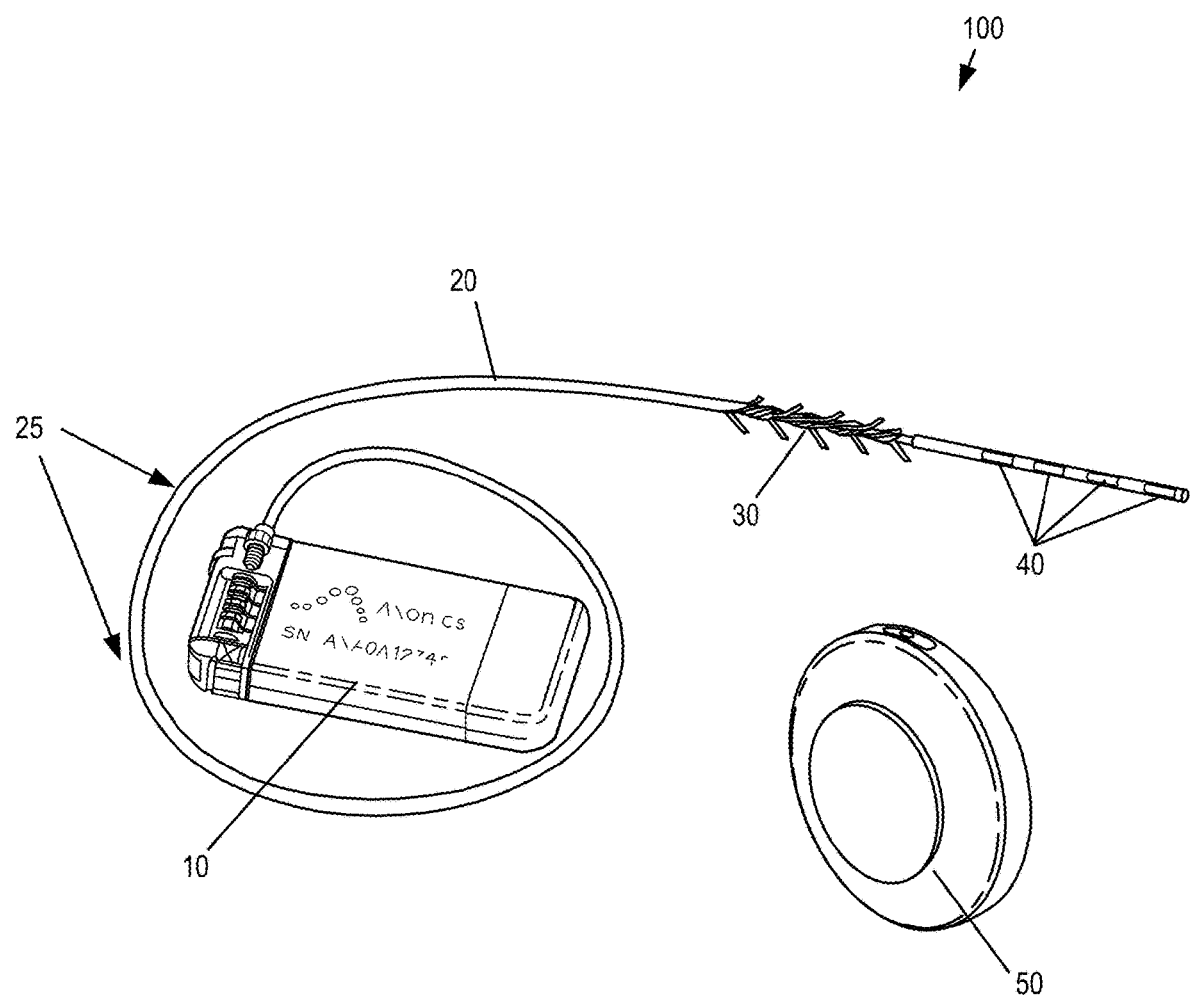
FIG. 3 illustrates an example of a neurostimulation system having an implantable stimulation lead, an implantable pulse generator, and an external charging device, in accordance with aspects of the invention.

FIG. 3 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes. In sacral nerve stimulation, the lead is typically implanted through the S3 foramen as described herein.

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be patched to the patient's skin using an adhesive or can be held in place using a belt 53 or by an adhesive patch 52, such as shown in the schematic of FIG. 1. The CD may be charged by plugging the CD directly into an outlet or by placing the CD in a charging dock or station 51 that connects to an AC wall outlet or other power source.

The system may further include a patient remote 70 and CP 60, each configured to wirelessly communicate with the implanted IPG, or with the EPG during a trial, as shown in the schematic of the nerve stimulation system in FIG. 1. The CP 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 10 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

Figure 4:
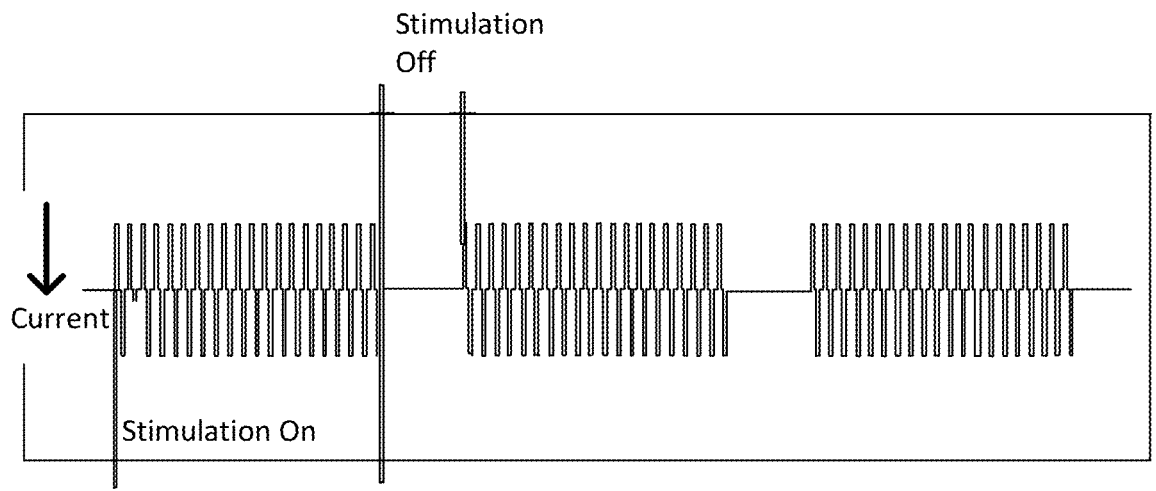
FIG. 4 illustrates an example of stimulation in a cycling mode, in which the duty cycle is the stimulation on time over the stimulation-on time plus the stimulation-off time.
Figure 5:
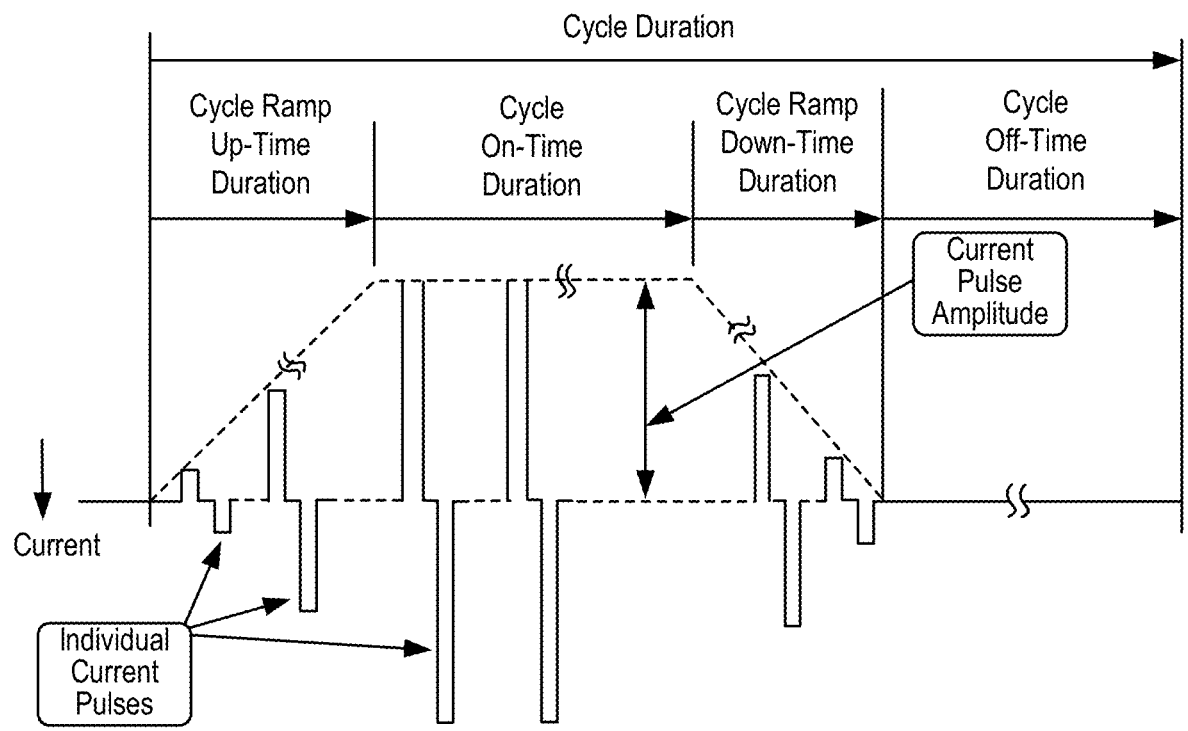
FIG. 5 illustrates signal characteristics of a neurostimulation program, exhibiting a ramping feature.

In one aspect, the CP 60 may be used to program the IPG/EPG according to various stimulation modes, which can be determined by the CP or selected by the physician using the CP. In some embodiments, the IPG/EPG may be configured with two stimulation modes: continuous mode and cycling mode. The cycling mode saves energy in comparison to the continuous mode, thereby extending the recharge interval of the battery and lifetime of the device. The cycling mode may also help reduce the risk of neural adaptation for some patients. Neural adaptation is a change over time in the responsiveness of the neural system to a constant stimulus. Thus, cycling mode may also mitigate neural adaptation so to provide longer-term therapeutic benefit. FIG. 4 illustrates an example of stimulation in a cycling mode, in which the duty cycle is the stimulation on time over the stimulation-on time plus the stimulation-off time. In some embodiments, the IPG/EPG is configured with a ramping feature, as shown in the example of FIG. 5. In these embodiments, the stimulation signal is ramped up and/or down between the stimulation-on and stimulation-off levels. This feature helps reduce the sudden "jolting" or "shocking" sensation that some patients might experience when the stimulation is initially turned on or at the cycle-on phase during the cycling mode. This feature is particularly of benefit for patients who need relative high stimulation settings and/or for patients who are sensitive to electrical stimulation.

To activate an axon of a nerve fiber, one needs to apply an electric field outside of the axon to create a voltage gradient across its membrane. This can be achieved by pumping charge between the electrodes of a stimulator. Action potentials, which transmit information through the nervous system, are generated when the outside of the nerve is depolarized to a certain threshold, which is determined by the amount of current delivered. To generate continuous action potentials in the axon, this extracellular gradient threshold needs to be reached with the delivery of each stimulation pulse.

In conventional systems, a constant voltage power source is able to maintain the output voltage of the electrodes, so that enough current is delivered to activate the axon at initial implantation. However, during the first several weeks following implantation, tissue encapsulation around electrodes occurs, which results in an impedance (tissue resistance) increase. According to the ohms' law (I=V/R where I is the current, V the voltage and R the tissue impedance of the electrode pair), current delivered by a constant voltage stimulator will therefore decrease, generating a smaller gradient around the nerve. When the impedance reaches a certain value, extracellular depolarization will go down below the threshold value, so that no more action potential can be generated in the axon. Patients will need to adjust the voltage of their system to re-adjust the current, and restore the efficacy of the therapy.

In contrast, embodiments of the present invention utilize a constant current power source. In one aspect, the system uses feedback to adjust the voltage in such a way that the current is maintained regardless of what happens to the impedance (until one hits the compliance limit of the device), so that the gradient field around the nerve is maintained overtime. Using a constant current stimulator keeps delivering the same current that is initially selected regardless the impedance change, for a maintained therapeutic efficacy.

Figure 6:
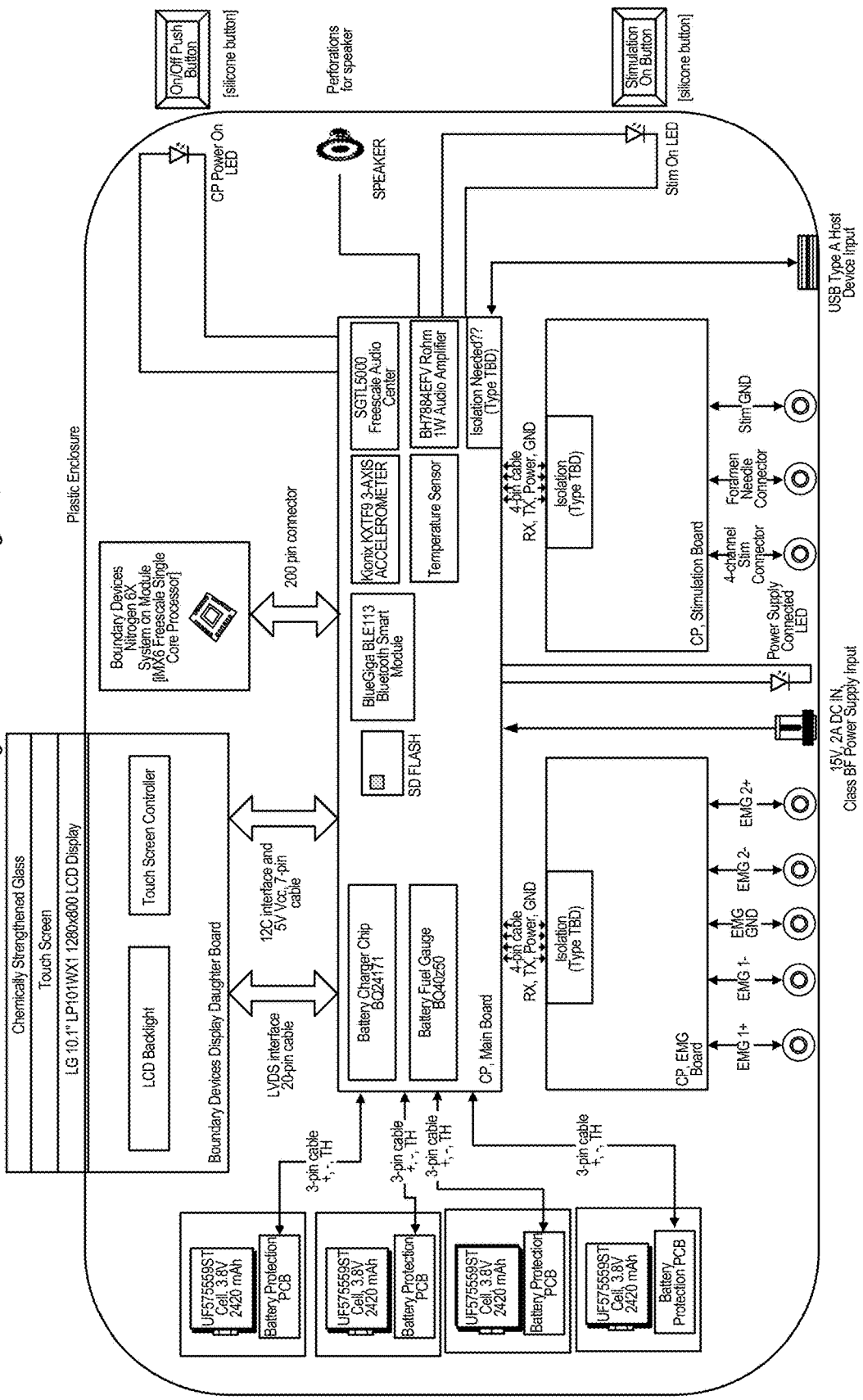
FIG. 6 illustrates a schematic of a clinician programmer configuration.

FIG. 6 schematically illustrates a block diagram of the configuration of the CP 60 and associated interfaces and internal components. As described above, CP 60 is typically a tablet computer with software that runs on a standard operating system. The CP 60 includes a communication module, a stimulation module and an EMG sensing module. The communication module communicates with the IPG and/or EPG in the medical implant communication service frequency band for programming the IPG and/or EPG. While this configuration reflects a portable user interface display device, such as a tablet computer, it is appreciated that the CP may be incorporated into various other types of computing devices, such as a laptop, desktop computer, or a standalone terminal for use in a medical facility.

III. Monitoring and Regulation of Temperature on Neurostimulator Programmers

In some embodiments, the temperature of neurostimulator programmers (for example, the CP 60 or the patient remote 70) may need to be monitored and/or regulated to abide by prescribed standards set by the manufacturer or by the regulating agency. For example, neurostimulator programmers may need to abide by safety and/or efficacy regulations that prescribe maximum temperatures or optimal temperatures that may be sustained by a neurostimulator programmer while it is in use. A neurostimulator programmer may include components that generate heat, and this heat may accumulate within the neurostimulator programmer such that it may exceed thresholds beyond which the neurostimulator programmer may not operate safely, or beyond which the neurostimulator programmer may not operate optimally. Moreover, in some instances, the environment in which the neurostimulator programmer may be operated may introduce heat. It is therefore advantageous for the neurostimulator programmer to make use of one or more temperature monitoring and/or regulating software algorithms to maintain safety and efficacy.

III.A) Example First Temperature-Regulation Software

Figure 7:
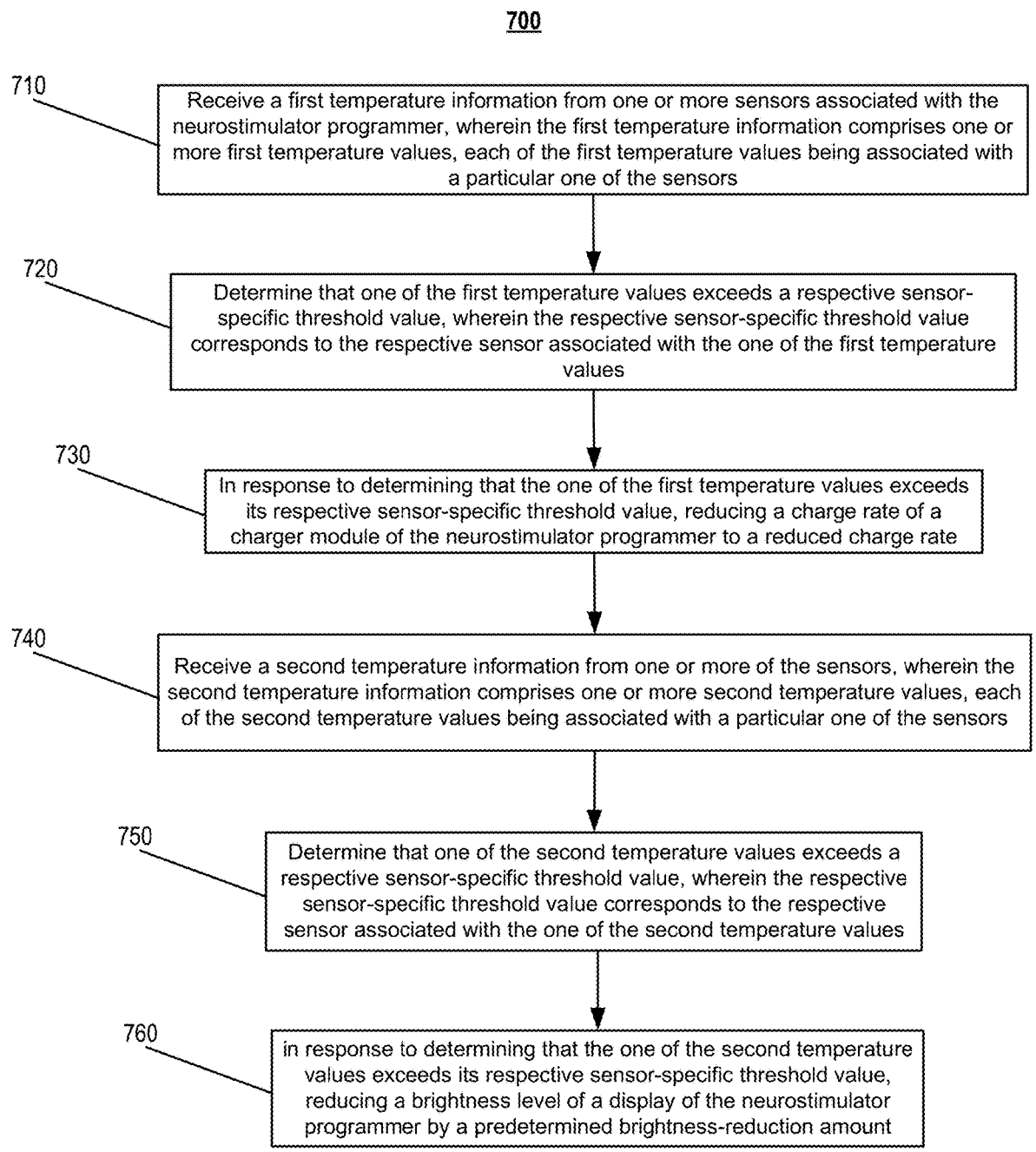
FIG. 7 illustrates an example method that may be executed by a first temperature-regulation software for monitoring temperature of the neurostimulator programmer and taking one or more steps to reduce the temperature if it is determined that the temperature is beyond one or more thresholds.

FIG. 7 illustrates an example method 700 that may be executed by a first temperature-regulation software for monitoring temperature of the neurostimulator programmer and taking one or more steps to reduce the temperature if it is determined that the temperature is beyond one or more thresholds. In some embodiments, this first temperature-regulation software may be implemented by one or more processors of the neurostimulator programmer, which may be disposed within a portable housing of the neurostimulator programmer. In some embodiments, as illustrated by step 710 in FIG. 7, the neurostimulator programmer may receive a first temperature information from one or more sensors associated with the neurostimulator programmer. The first temperature information may include one or more first temperature values, each of the first temperature values being associated with a particular one of the sensors.

Any suitable sensors of any suitable type may be used to measure temperature for generating the first temperature values. For example, the sensors may be thermistors (for example, Negative Temperature Coefficient (NTC) thermistors), resistance temperature detectors (RTD), thermocouples, and/or semi-conductor-based sensors. In some embodiments, the sensors may include a display sensor for sensing a temperature generated by a display of the neurostimulator programmer, a charger sensor for sensing a temperature generated by a charger module of the neurostimulator programmer, a CPU sensor for sensing a temperature generated by a CPU of the neurostimulator programmer, a battery sensor for sensing a temperature generated by a battery of the neurostimulator programmer as it is being discharged, and/or any other suitable sensors. In this example, each of these sensors may be disposed at or near a respective heat-generating component. For example, the display sensor may be disposed within the housing of the neurostimulator programmer near an inverter that powers the display (for example, near a cold-cathode fluorescent lamp (CCFL) of an LCD display), or near one or more LEDs of the display. As another example, the charger sensor may be disposed near the charger module of the neurostimulator programmer. As another example, the CPU sensor may be disposed at or near the CPU of the neurostimulator programmer. As another example, the battery sensor may be disposed at or near the battery pack of the neurostimulator programmer. In an example embodiment, the neurostimulator programmer may receive a first temperature information that may include a first temperature value associated with a display sensor and also a first temperature value associated with a charger sensor, indicating for example temperatures near the display inverter and the charger module, respectively.

Figure 8:
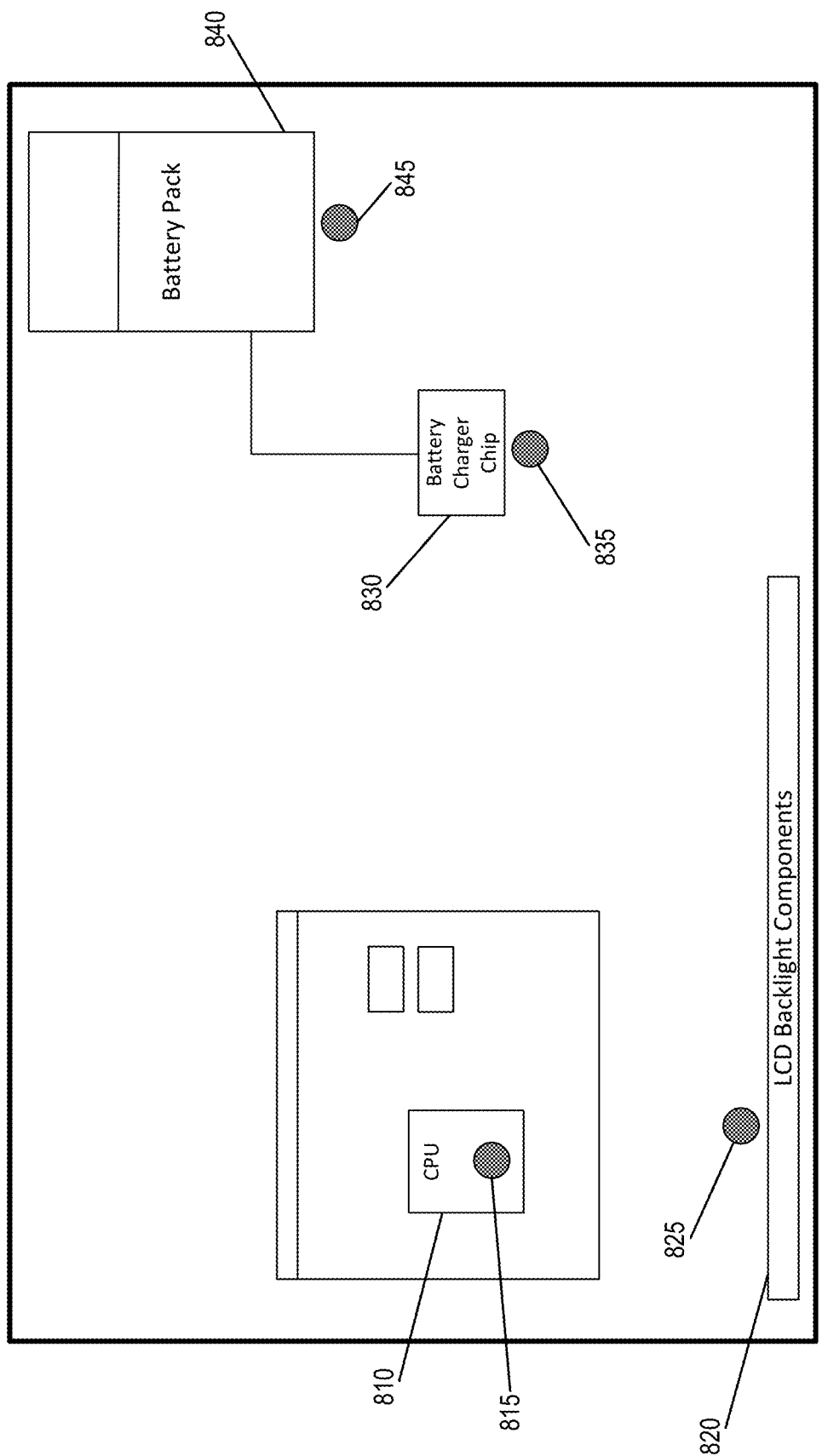
FIG. 8 illustrates an example schematic of a printed circuit board assembly (PCBA) of a neurostimulator programmer including an example set of sensors disposed in example locations.

FIG. 8 illustrates an example schematic of a printed circuit board assembly (PCBA) of a neurostimulator programmer including an example set of sensors disposed in example locations. In some embodiments, the PCBA may include a CPU sensor 815 that may be at or near a CPU 810. The CPU sensor 815 may be located such that it is suited for detecting heat generated by the CPU 810. In some embodiments, the PCBA may include a display sensor 825 that may be at or near one or more backlight components (for example, LCD backlight components 820) of the neurostimulator programmer. The backlight components may include, for example, an inverter and/or LEDs of the backlight. The display sensor 825 may be located such that it is suited for detecting heat generated by the display. In some embodiments, the PCBA may include a charger sensor 835 that may be at or near a charging module (for example, the battery charger chip 830). The charger sensor 835 may be located such that it is suited for detecting heat generated by the charging module as it, for example, steps down voltage, as described elsewhere herein. In some embodiments, the PCBA may include a battery sensor 845 that may be at or near a battery pack 840. The battery pack 840 may include one battery or several batteries that may be coupled together. The battery sensor 845 may be located such that it is suited for detecting heat generated by the charging or discharging of the battery pack 840 or components thereof. Although FIG. 8 illustrates a configuration that includes four different types of sensors (the CPU sensor 815, the display sensor 825, the charger sensor 835, and the battery sensor 845), this disclosure contemplates any number or combination of these types of sensors and/or any other suitable types of sensors. Moreover, although FIG. 8 illustrates only one sensor of each type (for example, only one battery sensor 845, only one display sensor 825) this disclosure contemplates that any suitable number of such sensors may be incorporated into the PCBA. For example, in a case where the battery pack includes four different batteries, there may be a battery sensor 845 adjacent to each of the four different batteries.

In some embodiments, as illustrated by step 720 in FIG. 7, the neurostimulator programmer may determine whether one of the first temperature values exceeds a threshold value. In some embodiments, each sensor may have a threshold value that is specific to the sensor—that is, each sensor may have a sensor-specific threshold value. For example, a sensor-specific threshold value corresponding to a display sensor may be about 45 degrees Celsius. As another example, a sensor-specific threshold value corresponding to the charger sensor may be about 42 degrees Celsius. As such, the determination as to whether a first temperature value exceeds a threshold value may require consideration of the sensor-specific threshold value associated with the sensor from which the first temperature value was measured. The neurostimulator programmer may thus determine whether any of the one or more first temperature values exceeds its respective sensor-specific threshold value.

In some embodiments, as illustrated by step 730 in FIG. 7, in response to a determination that one of the first temperature values exceeds its respective sensor-specific threshold value, the neurostimulator programmer may attempt to cause a reduction in temperature by performing a suitable temperature-reducing action. In attempting to reduce temperature, the neurostimulator programmer may, for example, reduce a functionality of a first heat-generating component, or multiple such components, of the neurostimulator programmer. Reducing functionality may serve to reduce the generation of heat by these components. In some embodiments, the neurostimulator programmer may reduce a charge rate of a charger module of the neurostimulator programmer to a reduced charge rate. The reduced charge rate may be a predetermined charge rate, for example, set at 25% of a maximum charge rate. In some embodiments, the neurostimulator programmer may reduce the charge rate by a predetermined amount. For example, the charge rate may be reduced by 20% of the maximum charge rate. Alternatively, the predetermined amount may vary based on the current charge rate of the neurostimulator programmer (for example, it may be set at 10% of the current charge rate).

In embodiments where the charge rate is reduced by a predetermined amount, the neurostimulator programmer may reduce the charge rate of the charger module incrementally. For example, the neurostimulator programmer may reduce the charge rate by 20% of the maximum charge rate, and may continue to do so until the charge rate reaches a minimum level (or until each of the second temperature values are at or below its respective sensor-specific threshold value). In this example, the neurostimulator programmer may reduce the charge rate until it reaches a minimum level of 25%. Alternatively, the neurostimulator programmer may reduce the charge rate until charging is disabled entirely. In some embodiments, the incremental reduction of charge rate may occur first before a brightness level of the display is reduced (the reduction of the rightness level is explained in further detail below). In other embodiments, the incremental reduction of charge rate may occur along with the reduction of the brightness level.

In some embodiments, the charger module may be a module within the neurostimulator programmer housing that receives at a port a coupling to a source of AC current (for example, an outlet) to charge a battery of the neurostimulator programmer. The charger module may, for example, convert the AC current into DC current for charging a battery pack of the neurostimulator programmer. This conversion process may generate heat that may accumulate within the neurostimulator programmer. In some embodiments, the charger module may receive DC current but the voltage of the current may need to be adjusted. For example, the charger module may step down the voltage to a level that is appropriate for charging the battery pack. In these embodiments, the adjustment of voltage may generate heat that may accumulate within the neurostimulator programmer. In some embodiments, the charger module may receive energy wirelessly from a source (for example, using induction technology), which may generate heat. In some embodiments, the manufacturer may determine that the reduction of the charge rate may be an optimal first step, at least in part because the manufacturer may determine that the reduction in charge rate may not impede the functionality of the neurostimulator programmer as a whole, relative to a reduction in functionality of other heat-generating components (for example, a display of the neurostimulator programmer).

In some embodiments, as illustrated by step 740 of FIG. 7, the neurostimulator programmer may receive a second temperature information from one or more of the sensors. The second temperature information may include one or more second temperature values, each of the second temperature values being associated with a particular one of the sensors. In some embodiments, the second temperature information may be received after the first temperature information is received. In some embodiments, the second temperature information may be received after a predetermined period of time elapses following a temperature-reducing action attempted by the neurostimulator programmer. In some embodiments, the predetermined period of time may be about 1 minute. For example, the second temperature information may be received after 1 minute elapses following the reduction of the charge rate of the neurostimulator programmer.

In some embodiments, as illustrated by step 750 of FIG. 7, the neurostimulator programmer may determine whether each of the second temperature values exceeds its respective sensor-specific threshold value corresponding to the associated sensor.

In some embodiments, as illustrated by step 760 of FIG. 7, in response to determining that a second temperature value exceeds its respective sensor-specific threshold value, the neurostimulator programmer may attempt to cause a reduction in temperature by performing another suitable action. In attempting to reduce temperature, the neurostimulator programmer may, for example, reduce a functionality of a second heat-generating component. For example, the second heat-generating component may be a display of the neurostimulator programmer, in which case the neurostimulator programmer may reduce a brightness level of the display. In this example, the neurostimulator programmer may reduce a brightness level of a display of the neurostimulator programmer by a predetermined brightness-reduction amount. The brightness-reduction amount may be any suitable amount. For example it may be set at 10% of the maximum brightness level. Alternatively, it may vary based on the current brightness level of the neurostimulator programmer (for example, it may be set at 10% of the current brightness level).

Figure 9A:
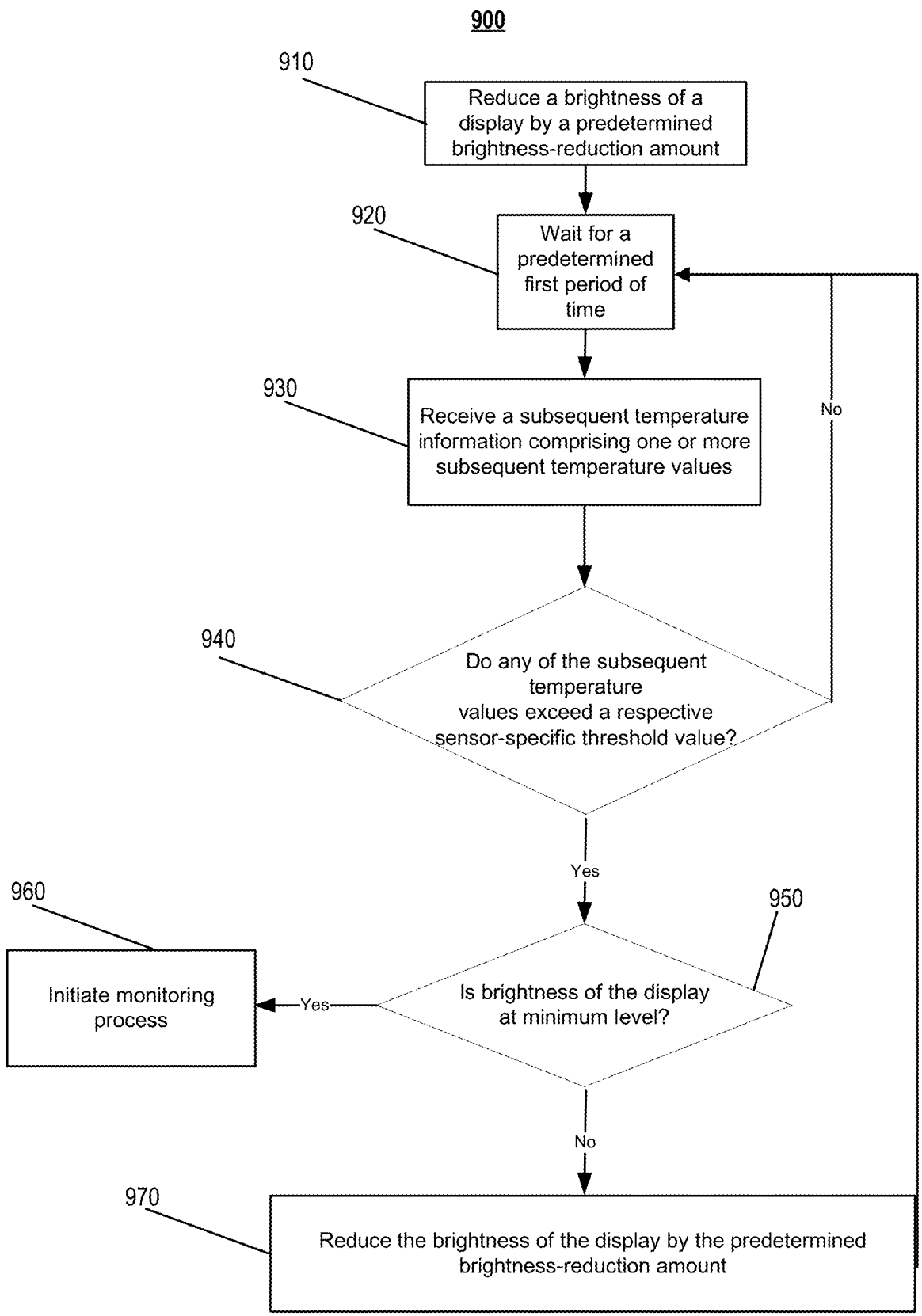
FIG. 9A illustrates an example method of a process in which the neurostimulator programmer reduces a brightness level of the display to reduce temperature.

FIG. 9A illustrates an example method 900 of a process in which the neurostimulator programmer reduces a brightness level of the display to reduce temperature. At step 910, the neurostimulator programmer may reduce a brightness of its display by a predetermined brightness-reduction amount.

At step 920, the neurostimulator programmer may wait for a predetermined first period of time (for example, 1 minute). At step 930, the neurostimulator programmer may receive, from one or more of the sensors, a subsequent temperature information that includes one or more subsequent temperature values. At step 940, the neurostimulator programmer may determine whether any of the subsequent temperature values exceeds their respective sensor-specific threshold values. If it is determined that each of the subsequent temperature values do not exceed their respective sensor-specific threshold values, the method 900 may loop back to step 920. However, if it is determined that at least one of the subsequent temperature values exceeds its respective sensor-specific threshold value, the method 900 may proceed to step 950. At step 950, the neurostimulator programmer may determine whether a current brightness level of the display is at a minimum brightness level. This minimum brightness level may be set by, for example, the manufacturer or by an operator of the neurostimulator programmer. For example, the minimum brightness level may be 10% of the maximum brightness level. If it is determined that the current brightness level of the display is already at the minimum brightness level, the method 900 may proceed to step 960, where the neurostimulator programmer may initiate a monitoring process (for example, as outlined below). However, if it is determined that the current brightness level of the display is not at the minimum brightness level, the method 900 may proceed to step 970, where the neurostimulator programmer may again reduce the brightness level of the display by the predetermined brightness-reduction amount. The method 900 may then loop back to step 920. In some embodiments, the method 900 may continue in this manner until the brightness level of the display reaches a minimum brightness level or until each of the subsequent temperature values is at or below its respective sensor-specific threshold value.

Figure 9B:
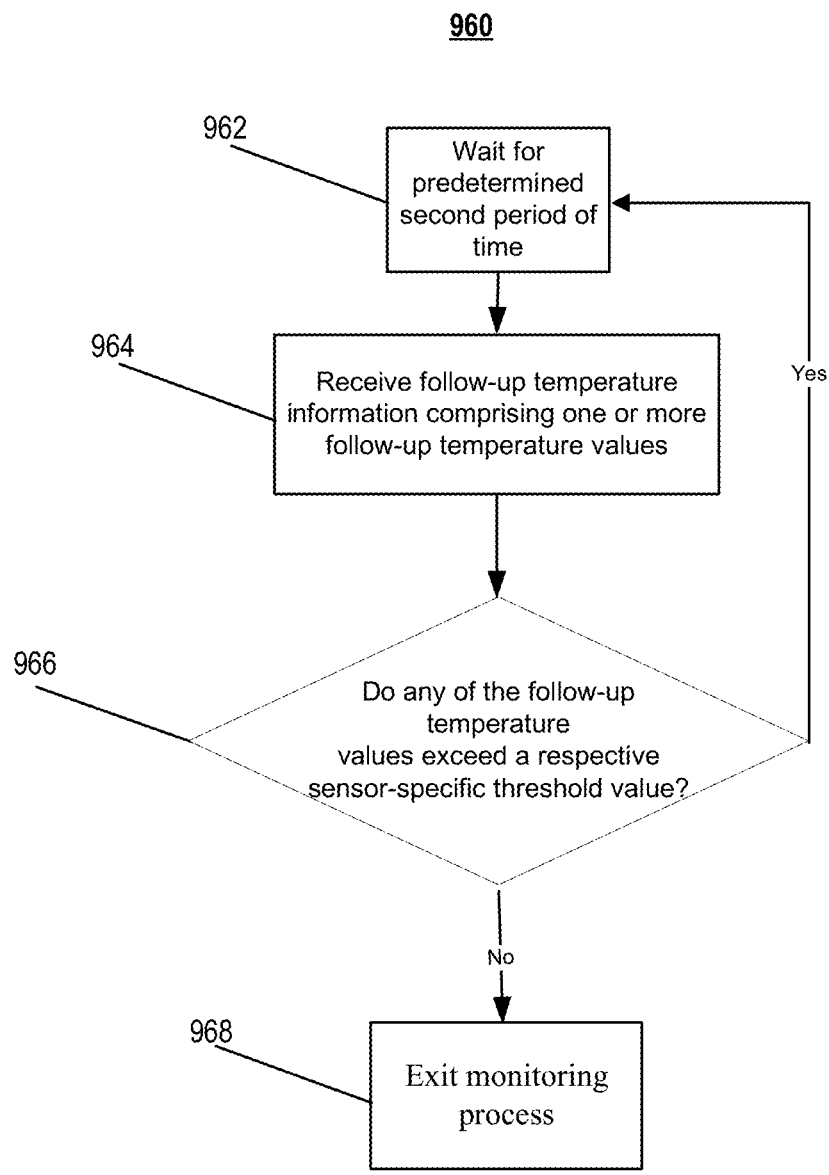
FIG. 9B illustrates an example method of a monitoring process in which the neurostimulator programmer monitors temperature values.

FIG. 9B illustrates an example method 960 of a monitoring process in which the neurostimulator programmer monitors temperature values. The method 960 may start at step 962, where the neurostimulator programmer may wait for a predetermined second period of time. In some embodiments, the predetermined second period of time may be less than the predetermined first period of time described with respect to step 920 of FIG. 9A. For example, the predetermined second period of time may be 10 seconds, whereas the predetermined first period of time may have been 1 minute. This may be, because the monitoring process may be correspond to a "high-alert condition," where the temperature of the neurostimulator programmer is high and yet the neurostimulator programmer is unable to reduce the brightness level so as to reduce the temperature. In such a condition, increased monitoring may be warranted. In some embodiments, when the neurostimulator programmer is in this high-alert condition, the neurostimulator programmer may provide an indication or an alarm/warning to an operator of the neurostimulator programmer. Referencing FIG. 9B, at step 964, the neurostimulator programmer may receive a follow-up temperature information that includes one or more follow-up temperature values. At step 966, the neurostimulator programmer may determine whether any of the follow-up temperature values exceeds its respective sensor-specific threshold value. If it is determined that at least one of the follow-up temperature values exceeds its respective sensor-specific threshold value, the method 960 may loop back to step 962. However, if it is determined that each of the follow-up temperature values is at or below its respective sensor-specific threshold value, the method 960 may proceed to step 968, where the neurostimulator programmer may exit the monitoring process.

In some embodiments, the neurostimulator programmer may receive second temperature values where each of the second temperature values is determined to be at or below its respective sensor-specific threshold value. In response, the neurostimulator programmer may reverse course taken by prior actions to reduce functionality. For example, in the case where a charge rate of the neurostimulator programmer was decreased, the neurostimulator programmer may increase the charge rate by a predetermined amount. In this example, it may then initiate a follow-up process that may monitor and continue to increase functionality so long as second temperature values remain at or below respective sensor-specific threshold values. For example, the follow-up process may include the steps of (a) waiting for a predetermined period of time; (b) receiving a follow-up temperature information from one or more of the sensors after waiting for the predetermined period of time, wherein the follow-up temperature information may include one or more follow-up temperature values; (c) determining whether each of the follow-up temperature values is below its respective sensor-specific threshold value; and (d) again increasing the charge rate by the predetermined amount if it is determined that each of the follow-up temperature values is below its respective sensor-specific threshold value. These steps may be repeated until the charge rate reaches a maximum charge rate (for example, 100%) or until one of the follow-up temperature values exceeds its respective sensor-specific threshold value.

Figure 10:
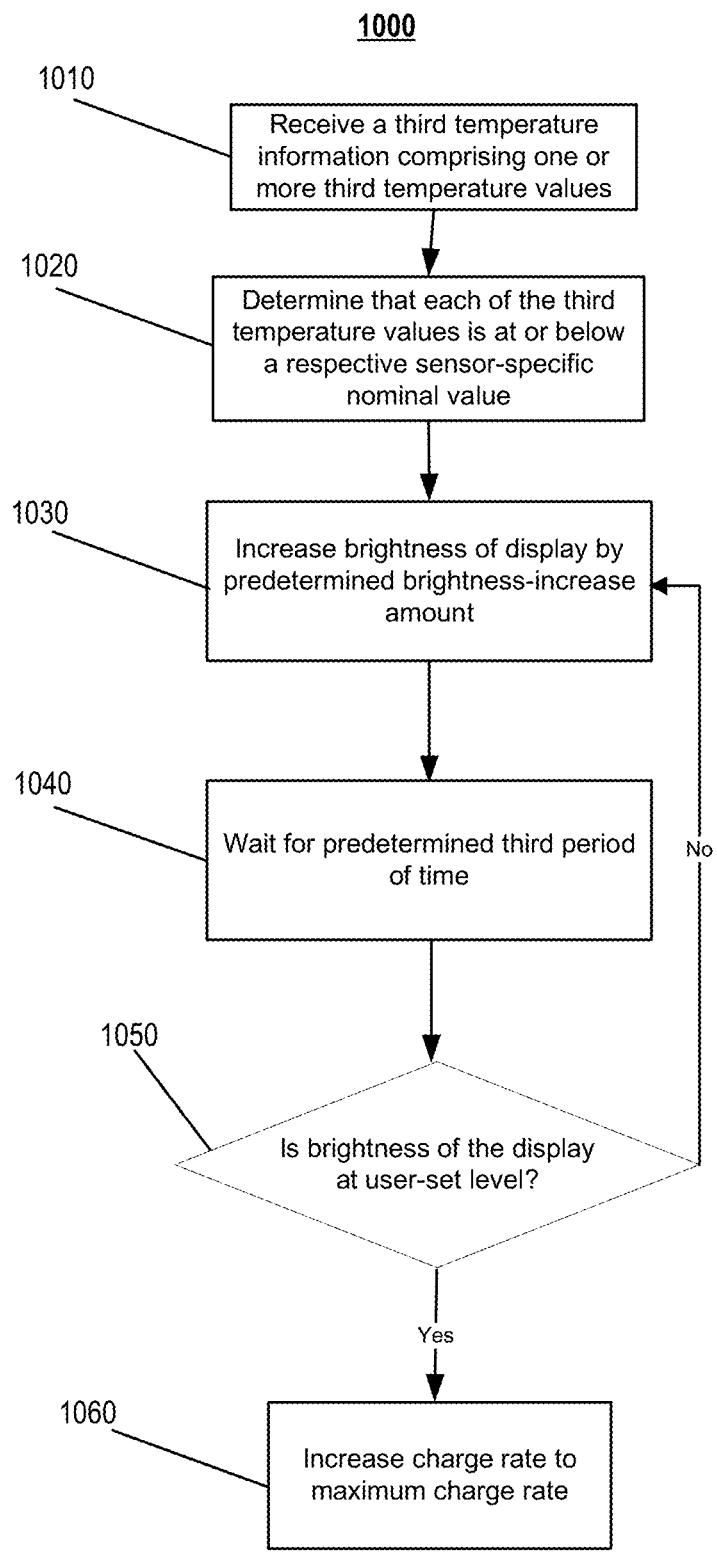
FIG. 10 illustrates an example method of a process in which the neurostimulator programmer increases a brightness level of the display only when it is determined that a temperature of the neurostimulator programmer is nominal again.

FIG. 10 illustrates an example method 1000 of a process in which the neurostimulator programmer increases a brightness level of the display only when it is determined that a temperature of the neurostimulator programmer is nominal again. The method 1000 may start at step 1010, where the neurostimulator may receive a third temperature information that includes one or more third temperature values. At step 1020 the neurostimulator programmer may determine that each of the third temperature values is at or below a respective sensor-specific nominal value. In some embodiments, the sensor-specific nominal value for a particular sensor may be different from the sensor-specific threshold value for the particular sensor. For example, the sensor-specific nominal value may be less than the sensor-specific threshold value. As an example, the sensor-specific nominal value of a display sensor may be around 42 degrees Celsius, as compared to a sensor-specific threshold value that may be around 45 degrees Celsius for the same display sensor. When the sensor-specific nominal value is reached, it may indicate that it is particularly safe to increase functionality of one or more heat-generating components of the neurostimulator programmer. Referring to FIG. 10, the method 1000 may proceed to step 1030, where the neurostimulator programmer may increase the brightness level of the display by a predetermined brightness-increase amount. In some embodiments, this brightness-increase amount may be equivalent to the brightness-reduction amount. For example, both the brightness-increase amount and the brightness-reduction amount may be 10% of the maximum brightness level of the display. In other embodiments, the brightness-increase amount may be different from the brightness-reduction amount. For example, the brightness-increase amount may be 5% of the maximum brightness level of the display, while the brightness-reduction amount may be 10% of the maximum brightness level of the display. The method 1000 may then proceed to step 1040, where the neurostimulator programmer may wait for a predetermined third period of time. In some embodiments, the third period of time may be around 1 minute. The method 1000 may then proceed to step 1050, where the neurostimulator programmer determines whether the current brightness level of the display is at a user-set level (alternatively, it may determine whether the current brightness level of the display is at a maximum brightness level). In the event of a negative determination, the method 1000 may loop back to step 1030, again causing an increase of the brightness level. However, in the event of a positive determination, the method 1000 may proceed to step 1060, where the neurostimulator programmer may increase a charge rate to a maximum charge rate. Alternatively, the neurostimulator programmer may increase the charge rate by a predetermined amount, and may incrementally increase the charge rate, waiting in between each increase, for example, for the predetermined third period of time.

Although the disclosure focuses on a particular order of actions for reducing temperature, with the first heat-generating component being the charger module and the second heat-generating component being the display, the disclosure contemplates any suitable order of actions. For example, the first heat-generating component may be the display and the second heat-generating component may be the charger module. In this example, the functionality of bird display may be reduced before the functionality of the charger module. Additionally, although the disclosure focuses on the display and the charger module as first and/or second heat-generating components for which functionality may be reduced, the disclosure contemplates reducing functionality for any other suitable heat-generating components (the CPU, the battery, etc.) in the neurostimulator programmer. This reduction may be performed additionally to or alternatively to the reduction of functionality of the charger module and/or the display. For example, in response to determining that a first or second temperature value exceeds a respective sensor-specific threshold value, the neurostimulator programmer may adjust a clock speed of its CPU (for example, reducing the clock speed of its CPU), or reduce power consumption of the neurostimulator programmer.

Additionally, although the disclosure focuses on reducing one or more functionalities, the disclosure also contemplates other types of actions that may reduce overall temperature of the neurostimulator programmer. In some embodiments, the neurostimulator programmer may turn on or increase a functionality of a heatsink or heat exchanger device such as a fan component of the neurostimulator programmer (for example, increasing the speed of the fan component). Such an increase in functionality may be performed additionally or alternatively to the reduction of functionality described elsewhere. For example, in response to determining that a second temperature value exceeds its respective sensor-specific threshold value, rather than (or in addition to) reducing the brightness level of the display, the neurostimulator programmer may turn on or increase the speed of a fan component in an attempt to reduce the temperature of the neurostimulator programmer.

III.B) Example Second Temperature-Regulation Software

In some embodiments, a neurostimulator programmer may alternatively or additionally implement a second temperature-regulation software that may be capable of shutting down the neurostimulator programmer if a temperature of the neurostimulator programmer is beyond one or more thresholds. In some embodiments, the second temperature-regulation software may provide a final safety net in cases where particularly excessive temperatures are reached. In some embodiments, this second temperature-regulation software may be implemented to run simultaneously with the first temperature-regulation software. In some embodiments, the second temperature-regulation software may operate independently of the first temperature-regulation software.

Figure 11:
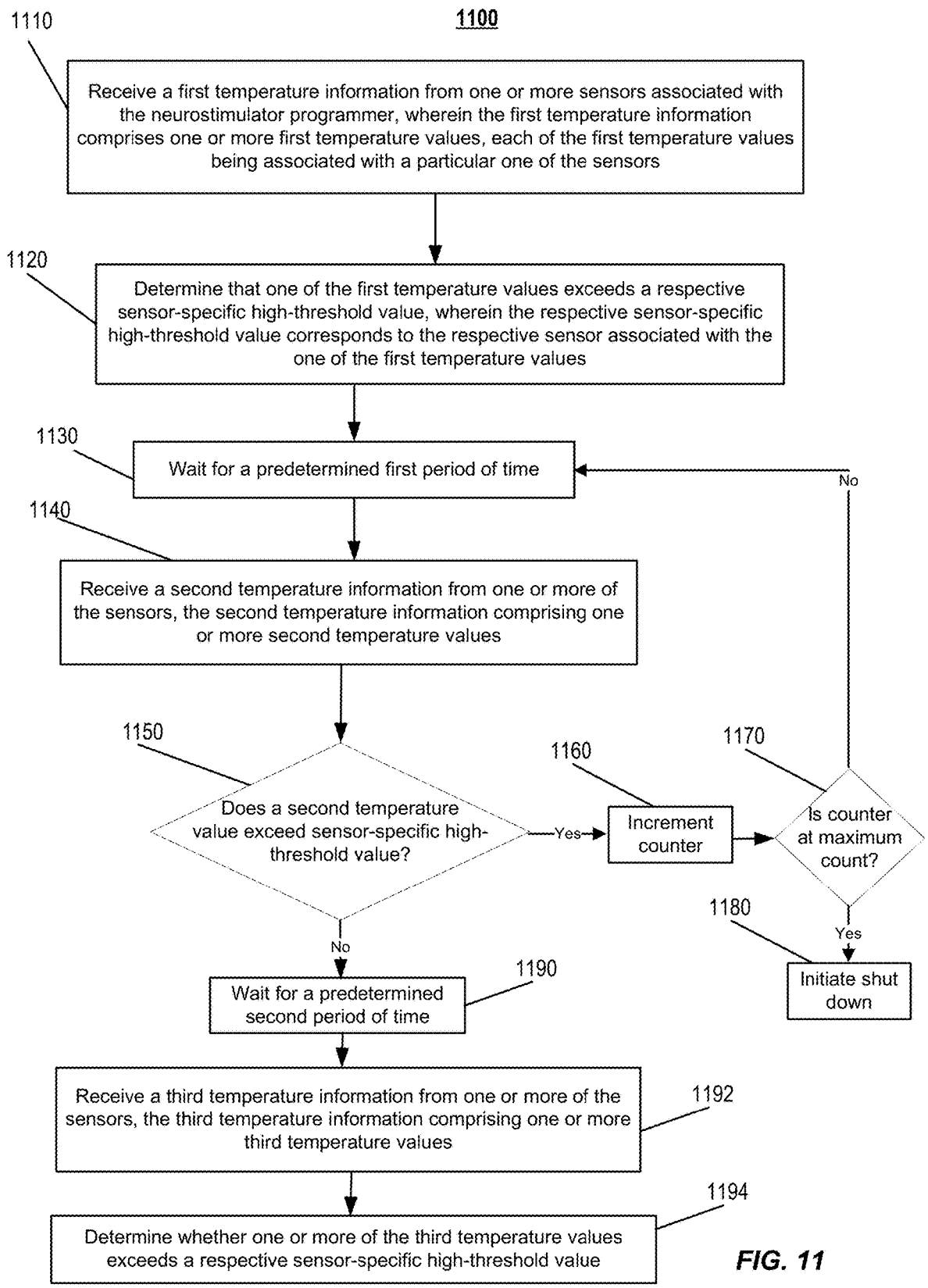
FIG. 11 illustrates an example method that may be executed by a second temperature-regulation software for monitoring temperature of the neurostimulator programmer and shutting down the neurostimulator programmer if it is determined that the temperature is beyond one or more thresholds.

FIG. 11 illustrates an example method 1100 that may be executed by a second temperature-regulation software for monitoring temperature of the neurostimulator programmer and shutting down the neurostimulator programmer if it is determined that the temperature is beyond one or more thresholds. In some embodiments, this first temperature-regulation software may be implemented by one or more processors of the neurostimulator programmer, which may be disposed within a housing of the neurostimulator programmer. In some embodiments, as illustrated by step 1110 in FIG. 11, the neurostimulator programmer may receive a first temperature information from one or more sensors associated with the neurostimulator programmer. The first temperature information comprises one or more first temperature values, each of the first temperature values being associated with a particular one of the sensors.

In some embodiments, as illustrated by step 1120 of FIG. 11, the neurostimulator programmer may determine whether one of the first temperature values exceeds a respective sensor-specific high-threshold value. Each respective sensor-specific high-threshold value may corresponds to a respective sensor associated with one of the first temperature values. In some embodiments, the respective sensor-specific high-threshold values may indicate an unsafe operating temperature. In some embodiments, the respective sensor-specific high-threshold values may be higher than their counterpart sensor-specific threshold values, as described herein with respect to the first temperature-regulation software. For example, a display sensor (for example, a display sensor disposed near a CCFL backlight inverter that powers an LCD display of the neurostimulator programmer) may have a sensor-specific high-threshold value of about 50 degrees Celsius, whereas the same display sensor may have a sensor-specific threshold value of about 45 degrees Celsius. As another example, a charger sensor disposed near a charger module of the neurostimulator programmer may have a sensor-specific high-threshold value of about 55 degrees Celsius, whereas the same charger sensor may have a sensor-specific threshold value of about 44 degrees Celsius. In some embodiments, the second temperature-regulation software may receive temperature values from more sensors than the first temperature-regulation software. As an example, the first temperature-regulation software may only receive temperature values from a display sensor and a charger sensor, while the second temperature-regulation software may receive temperature values from the display sensor, the charger sensor, a CPU sensor, and a battery sensor. In this example, each of these sensors may be associated with their own sensor-specific high-threshold values. For example, the display sensor may be associated with a sensor-specific high-threshold value of about 50 degrees Celsius, the charger sensor may be associated with a sensor-specific high-threshold value of about 55 degrees Celsius, the CPU sensor may be associated with a sensor-specific high-threshold value of about 90 degrees Celsius, and the battery sensor may be associated with a sensor-specific high-threshold value of about 45 degrees Celsius.

In some embodiments, as illustrated by step 1130 of FIG. 11, in response to determining that at least one of the first temperature values exceeds its respective sensor-specific high-threshold value, the neurostimulator programmer may wait for a predetermined first period of time. As an example, the predetermined first period of time may be about 10 seconds. In some embodiments, this predetermined first period of time of the second temperature-regulation software may be a shorter period of time than the predetermined first period of time of the first temperature-regulation software. This may be the case because temperatures that exceed one or more of the sensor-specific high-threshold values may be particularly excessive (for example, relative to the sensor-specific threshold values of the first temperature-regulation software), and may require more frequent monitoring as a result.

In some embodiments, as illustrated by step 1140 of FIG. 11, after waiting for the predetermined first period of time, the neurostimulator programmer may receive a second temperature information from one or more of the sensors. The second temperature information may include one or more second temperature values.

In some embodiments, as illustrated by step 1150 of FIG. 11, the neurostimulator programmer may determine whether one of the second temperature values exceeds a respective sensor-specific high-threshold value. In some embodiments, if it is determined that at least one of the second temperature values exceeds its respective sensor-specific high-threshold value, the neurostimulator programmer may repeat steps 1130 to 1150. In some embodiments, the neurostimulator programmer may repeat these steps for a predetermined maximum number of times until each of the second temperature values is at or below its respective sensor-specific high-threshold value. The predetermined maximum number of times may dictate a maximum number of times that steps 1130 to 1150 may be performed consecutively. As an example, the predetermined maximum number of times may be 5 times. The neurostimulator programmer may then determine whether any of the second temperature values exceeds a respective sensor-specific high-threshold value. In some embodiments, a counter algorithm may be used to keep track of the number of times steps 1130 to 1150 are repeated. As illustrated by step 1160 of FIG. 11, for example, a counter may be incremented (or initialized if it has not already been initialized) when it is determined at step 1150 that at least one second temperature value exceeds its respective sensor-specific high-threshold value. At step 1170 of FIG. 11, the neurostimulator programmer may determine whether the counter is at a predetermined maximum count. In some embodiments, the maximum count may correspond to the predetermined maximum number of times that steps 1130 to 1150 may be repeated consecutively. If the counter is in fact at the predetermined maximum count, the neurostimulator programmer may initiate a shutdown of the neurostimulation programmer. In some embodiments, instead of initiating a shutdown, the neurostimulator may initiate a sleep or hibernation mode that may reduce all functionality of the device short of shutting down. However, if the counter is not yet at the maximum count, the method 1100 may loop back to step 1130, and steps 1130 to 1150 be repeated consecutively until the count reaches the maximum count or until none of the second temperature values exceed their respective sensor-specific high-threshold values. In some embodiments, the counter may be initialized to have a value corresponding to the predetermined maximum count, in which case the counter may be decremented each time the method 1100 loops back to step 1130. In this example, steps 1130 to 1150 may be repeated consecutively until the count reaches a minimum count (for example, a count of 0) or until none of the second temperature values exceed their respective sensor-specific high-threshold values.

In some embodiments, if none of the second temperature values exceed their respective sensor-specific high-threshold values, as illustrated in FIG. 11, the method 1100 may proceed to step 1190, where the neurostimulator programmer may wait for a predetermined second period of time. In some embodiments, the predetermined second period of time may be different from the predetermined first period of time. For example, the predetermined first period of time may be less than the predetermined second period of time. In this example, the predetermined first period of time may be about 10 seconds, while the predetermined second period of time may be about 1 minute. In some embodiments, after waiting for the predetermined second period of time, the neurostimulator programmer may receive a third temperature information from one or more of the sensors, as illustrated by step 1192 in FIG. 11. The third temperature information may include one or more third temperature values. As illustrated by step 1194 in FIG. 11, the neurostimulator programmer may determine whether one or more of the third temperature values exceeds a respective sensor-specific high-threshold value.

In some embodiments, where the first temperature-regulation software and the second temperature-regulation software are both being executed on a neurostimulator programmer, the second temperature-regulation software may override the first temperature-regulation software. For example, when a sensor-specific high-threshold value has been exceeded, the steps of the second temperature-regulation software may take precedence over the steps of the first temperature-regulation software. However, in some embodiments, the steps of both the first temperature-regulation software and the second temperature-regulation software may still continue to be performed in these cases. For example, the brightness level may be decreased according to the first temperature-regulation software, even as the second-temperature software is incrementing its counter on the way to a shutdown of the neurostimulator programmer. In other embodiments, the first temperature-regulation software may be halted when a sensor-specific high-threshold value has been exceeded, while the second temperature-regulation software may continue to execute.

Particular embodiments may repeat one or more steps of the methods of FIGS. 8-11, where appropriate. Although this disclosure describes and illustrates particular steps of the methods of FIGS. 8-11 as occurring in a particular order, this disclosure contemplates any suitable steps of the methods of FIGS. 8-11 occurring in any suitable order. Moreover, although this disclosure describes and illustrates example methods for regulating temperature of the neurostimulator programmer including the particular steps of the methods of FIGS. 8-11, this disclosure contemplates any suitable method for regulating temperature of a similar device including any suitable steps, which may include all, some, or none of the steps of the methods of FIGS. 8-11, where appropriate. For example, the disclosure contemplates that at least some of the steps of these methods may be optional, where appropriate. Furthermore, although this disclosure describes and illustrates particular components, devices, or systems carrying out particular steps of the methods of FIGS. 8-11, this disclosure contemplates any suitable combination of any suitable components, devices, or systems carrying out any suitable steps of the methods of FIGS. 8-11.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method for regulating temperature on a neurostimulator programmer configured to communicate with a neurostimulator device, the method comprising:
   receiving, by one or more processors, a first temperature information from one or more sensors associated with the neurostimulator programmer, wherein the first temperature information comprises one or more first temperature values, each of the first temperature values being associated with a particular one of the sensors;
   determining, by one or more of the processors, that one of the first temperature values exceeds a respective sensor-specific threshold value, wherein the respective sensor-specific threshold value corresponds to the respective sensor associated with the one of the first temperature values;
   in response to determining that the one of the first temperature values exceeds its respective sensor-specific threshold value, reducing a charge rate of a charger module of the neurostimulator programmer to a reduced charge rate; and
   receiving, by one or more of the processors, a second temperature information from the one or more of the sensors so as to continue temperature monitoring of the neurostimulator programmer, wherein the second temperature information comprises one or more second temperature values, each of the second temperature values being associated with a particular one of the sensors;
   wherein the charge rate is reduced continuously until the charge rate reaches a minimum level or until each of the second temperature values are at or below its respective sensor-specific threshold value.

2. The method of claim 1, wherein the one or more sensors comprises a display sensor disposed within a housing of the neurostimulator programmer, the display sensor being disposed near an inverter that powers a display of the neurostimulator programmer.

3. The method of claim 2, wherein the inverter is a cold-cathode fluorescent lamp (CCFL) backlight inverter, and wherein the display is an LCD display.

4. The method of claim 2, wherein the respective sensor-specific threshold value corresponding to the display sensor is about 45 degrees Celsius.

5. The method of claim 1, wherein the one or more sensors comprises a charger sensor disposed near the charger module of the neurostimulator programmer.

6. The method of claim 5, wherein the respective sensor-specific threshold value corresponding to the charger sensor is about 42 degrees Celsius.

7. The method of claim 1, wherein the first temperature information comprises a first temperature value associated with a first sensor disposed near an inverter that powers a display of the neurostimulator programmer, and further comprises a first temperature value associated with a second sensor disposed at a different location.

8. The method of claim 7, wherein the second sensor is disposed near the charger module of the neurostimulator programmer.

9. The method of claim 1, wherein the first temperature information comprises a first temperature value associated with a sensor disposed near a CPU of the neurostimulator programmer, further comprising:
   adjusting a clock speed of the CPU based on the first temperature value.

10. The method of claim 1, wherein the first temperature information comprises a first temperature value associated with a sensor disposed near a battery of the neurostimulator programmer.

11. The method of claim 1, wherein the respective sensor associated with the one of the first temperature values is the same as the respective sensor associated with the one of the second temperature values.

12. The method of claim 1, wherein the reduced charge rate is 25% of a maximum charge rate.

13. The method of claim 1, wherein the second temperature information is received after a predetermined first period of time elapses after reducing the charge rate of the charger module.

14. The method of claim 13, wherein the predetermined first period of time is about 1 minute.

15. The method of claim 1, further comprising:
   determining that each of the second temperature values is at or below a respective sensor-specific threshold value, wherein each respective sensor-specific threshold value corresponds to the respective sensor associated with one of the second temperature values; and
   in response to determining that each of the second temperature values is at or below its respective sensor-specific threshold value, increasing the charge rate by a predetermined amount, and initiating a follow-up process comprising:
   (a) waiting for a predetermined period of time;
   (b) receiving a follow-up temperature information from one or more of the sensors after waiting for the predetermined period of time, wherein the follow-up temperature information comprises one or more follow-up temperature values;
   (c) determining that each of the follow-up temperature values is below its respective sensor-specific threshold value;
   (d) increasing the charge rate by the predetermined amount; and
   (e) repeating steps (a) (d) until the charge rate reaches a maximum charge rate or until one of the follow-up temperature values exceeds its respective sensor-specific threshold value.

16. The method of claim 1, further comprising:
   determining that one of the second temperature values exceeds a respective sensor-specific threshold value, wherein the respective sensor-specific threshold value corresponds to the respective sensor associated with the one of the second temperature values; and
   in response to determining that the one of the second temperature values exceeds its respective sensor-specific threshold value, reducing a brightness level of a display of the neurostimulator programmer by a predetermined brightness-reduction amount.

17. The method of claim 16, wherein the predetermined brightness-reduction amount is 10% of a maximum brightness level.

18. A method for regulating temperature on a neurostimulator programmer configured to communicate with a neurostimulator device, the method comprising:
   receiving, by one or more processors, a first temperature information from one or more sensors associated with the neurostimulator programmer, wherein the first temperature information comprises one or more first temperature values, each of the first temperature values being associated with a particular one of the sensors;

determining, by one or more of the processors, that one of the first temperature values exceeds a respective sensor-specific threshold value, wherein the respective sensor-specific threshold value corresponds to the respective sensor associated with the one of the first temperature values;

in response to determining that the one of the first temperature values exceeds its respective sensor-specific threshold value, reducing a charge rate of a charger module of the neurostimulator programmer to a reduced charge rate;

receiving, by one or more of the processors, a second temperature information from the one or more of the sensors so as to continue temperature monitoring of the neurostimulator programmer, wherein the second temperature information comprises one or more second temperature values, each of the second temperature values being associated with a particular one of the sensors;

determining that one of the second temperature values exceeds a respective sensor-specific threshold value, wherein the respective sensor-specific threshold value corresponds to the respective sensor associated with the one of the second temperature values;

in response to determining that the one of the second temperature values exceeds its respective sensor-specific threshold value, reducing a brightness level of a display of the neurostimulator programmer by a predetermined brightness-reduction amount; and after reducing the brightness level of the display in response to determining that the one of the second temperature values exceeds its respective sensor-specific threshold value;

(a) waiting for a predetermined first period of time;

(b) receiving a subsequent temperature information from one or more of the sensors after waiting for the predetermined first period of time, wherein the subsequent temperature information comprises one or more subsequent temperature values;

(c) determining that one of the subsequent temperature values exceeds a respective sensor-specific threshold value;

(d) in response to determining that the one of the subsequent temperature values exceeds its respective sensor-specific threshold value, reducing the brightness level of a display of the neurostimulator programmer by the predetermined brightness-reduction amount; and (e) repeating steps (a) (d) until the brightness level of the display reaches a minimum brightness level or until each of the subsequent temperature values is at or below its respective sensor-specific threshold value.

19. The method of claim 18, further comprising in response to determining that the brightness level of the display has reached the minimum brightness level, initiating a continuous monitoring process, the continuous monitoring process comprising:

(a) waiting for a predetermined second period of time, wherein the predetermined second period of time is less than the predetermined first period of time;

(b) receiving a follow-up temperature information from one or more of the sensors after waiting for the predetermined second period of time, wherein the follow-up temperature information comprises one or more follow-up temperature values; and (c) repeating steps (a)-(b) until each of the follow-up temperature values is at or below its respective sensor-specific threshold values.

20. The method of claim 19, wherein the predetermined second period of time is about 10 seconds.

21. A method for regulating temperature on a neurostimulator programmer configured to communicate with a neurostimulator device, the method comprising:

receiving, by one or more processors, a first temperature information from one or more sensors associated with the neurostimulator programmer, wherein the first temperature information comprises one or more first temperature values, each of the first temperature values being associated with a particular one of the sensors;

determining, by one or more of the processors, that one of the first temperature values exceeds a respective sensor-specific threshold value, wherein the respective sensor-specific threshold value corresponds to the respective sensor associated with the one of the first temperature values;

in response to determining that the one of the first temperature values exceeds its respective sensor-specific threshold value, reducing a charge rate of a charger module of the neurostimulator programmer to a reduced charge rate;

receiving, by one or more of the processors, a second temperature information from the one or more of the sensors so as to continue temperature monitoring of the neurostimulator programmer, wherein the second temperature information comprises one or more second temperature values, each of the second temperature values being associated with a particular one of the sensors;

determining that one of the second temperature values exceeds a respective sensor-specific threshold value, wherein the respective sensor-specific threshold value corresponds to the respective sensor associated with the one of the second temperature values;

in response to determining that the one of the second temperature values exceed its respective sensor-specific threshold value, reducing a brightness level of a display of the neurostimulator programmer by a predetermined brightness-reduction amount;

(a) receiving a third temperature information from one or more of the sensors comprising one or more third temperature values;

(b) determining that each of the third temperature values is at or below a respective sensor-specific nominal value;

(c) in response to determining that each of the third temperature values is at or below its respective sensor-specific nominal value, increasing the brightness level of the display by a predetermined brightness-increase amount;

(d) waiting for a predetermined third period of time after increasing the brightness level of the display; and (e) repeating steps (a)-(d) until the brightness level of the display reaches a user-set level.

22. The method of claim 21, wherein the predetermined third period of time is about 1 minute.

23. The method of claim 21, further comprising increasing the charge rate of the charger module after the brightness level of the display reaches the user-set level.

24. The method of claim 23, wherein the charge rate of the charger module is increased to a maximum charge rate.

25. The method of claim 21, wherein the brightness-increase amount is the same as the brightness-reduction amount.

26. The method of claim 21, wherein the one or more sensors comprises a particular sensor disposed within a housing of the neurostimulator programmer, the particular sensor being disposed near an inverter that powers a display of the neurostimulator programmer, and wherein the respective sensor-specific nominal value of the particular sensor is about 42 degrees Celsius.

27. The method of claim 21, further comprising:
receiving a fourth temperature information from one or more of the sensors, wherein the fourth temperature information comprises one or more fourth temperature values, each of the fourth temperature values being associated with a particular one of the sensors;
corresponds to the respective sensor associated with the one of the fourth temperature values; and
in response to determining that the one of the fourth temperature values exceeds its respective sensor-specific high-threshold value,
(a) waiting for a predetermined period of time;
(b) after waiting for the predetermined period of time, receiving a subsequent temperature information from one or more of the sensors, the subsequent temperature information comprising one or more subsequent temperature values;
(c) determining whether one of the subsequent temperature values exceeds a respective sensor-specific high-threshold value; and
(d) repeating steps (a)-(c) for a predetermined maximum number of times or until each of the subsequent temperature values is at or below its respective sensor-specific high-threshold value.

28. A system for regulating temperature on a neurostimulator programmer configured to communicate with a neurostimulator device, the system comprising:
a neurostimulator device; and
a neurostimulator programmer comprising:
a portable housing;
one or more sensors for sensing temperature; and
one or more processors disposed within the portable housing configured to:
receive a first temperature information from one or more of the sensors, wherein the first temperature information comprises one or more first temperature values, each of the first temperature values being associated with a particular one of the sensors;
determine that one of the first temperature values exceeds a respective sensor-specific threshold value, wherein the respective sensor-specific threshold value corresponds to the respective sensor associated with the one of the first temperature values;
in response to determining that the one of the first temperature values exceeds its respective sensor-specific threshold value, reduce a charge rate of a charger module of the neurostimulator programmer to a reduced charge rate; and
receive a second temperature information from one or more of the sensors so as to continue temperature monitoring of the neurostimulator programmer, wherein the second temperature information comprises one or more second temperature values, each of the second temperature values being associated with a particular one of the sensors;
wherein the charge rate is reduced continuously until the charge rate reaches a minimum level or until each of the second temperature values are at or below its respective sensor-specific threshold value.

* * * * *